(12) United States Patent
Gibby et al.

(10) Patent No.: US 11,287,874 B2
(45) Date of Patent: Mar. 29, 2022

(54) USING OPTICAL CODES WITH AUGMENTED REALITY DISPLAYS

(71) Applicant: Novarad Corporation, American Fork, UT (US)

(72) Inventors: Wendell Arlen Gibby, Mapleton, UT (US); Steven Todd Cvetko, Draper, UT (US)

(73) Assignee: Novarad Corporation, American Fork, UT (US)

( * ) Notice: Subject to any disclaimer, the term of this patent is extended or adjusted under 35 U.S.C. 154(b) by 545 days.

(21) Appl. No.: 16/194,333

(22) Filed: Nov. 17, 2018

(65) Prior Publication Data
US 2020/0159313 A1    May 21, 2020

(51) Int. Cl.
| | |
|---|---|
| G06F 3/00 | (2006.01) |
| G06F 3/01 | (2006.01) |
| A61B 34/20 | (2016.01) |
| A61B 90/00 | (2016.01) |
| G02B 27/01 | (2006.01) |
| H04N 21/4405 | (2011.01) |

(Continued)

(52) U.S. Cl.
CPC ............. *G06F 3/011* (2013.01); *A61B 34/20* (2016.02); *A61B 90/36* (2016.02); *G02B 27/0172* (2013.01); *G06T 19/006* (2013.01); *H04N 21/4405* (2013.01); *A61B 2034/107* (2016.02); *A61B 2034/2055* (2016.02)

(58) Field of Classification Search
None
See application file for complete search history.

(56) References Cited

U.S. PATENT DOCUMENTS

| | | |
|---|---|---|
| 6,919,867 B2 | 7/2005 | Sauer |
| 8,657,809 B2 | 2/2014 | Schoepp |
| 9,119,655 B2 | 9/2015 | Bowling et al. |

(Continued)

FOREIGN PATENT DOCUMENTS

| | | |
|---|---|---|
| EP | 3470006 | 4/2019 |
| WO | WO 2008/076079 | 6/2008 |

(Continued)

OTHER PUBLICATIONS

US 9,980,782, 05/2018, Novarad Corporation (withdrawn).

(Continued)

*Primary Examiner* — Martin Mushambo
(74) *Attorney, Agent, or Firm* — Thorpe North and Western, LLP

(57) ABSTRACT

A technology is described for using a medical implement or a fluoroscopic image with reference to an image data set and a body of a person. A method may include detecting visual image data of a body of a patient and a medical implement. The optical codes on the body of the patient and on the medical implement may be identified. One operation is aligning the image data set with the body of the person using one or more optical codes on the body of the person and the fixed position of an image visible marker with respect to the optical code. A position of the medical implement with respect to the body of the person may be determined using one or more optical codes on the medical implement and the body of the person to reference the medical implement to the image data set and the body of the person.

29 Claims, 13 Drawing Sheets

(51) Int. Cl.
  *G06T 19/00* (2011.01)
  *A61B 34/10* (2016.01)

(56) References Cited

U.S. PATENT DOCUMENTS

| | | |
|---|---|---|
| 9,123,155 B2 | 9/2015 | Cunningham et al. |
| 9,128,909 B2 | 9/2015 | Brindley |
| 9,161,824 B2 | 10/2015 | Chishti |
| 9,861,446 B2 | 1/2018 | Lang |
| 9,980,780 B2 | 5/2018 | Lang |
| 10,154,239 B2 | 12/2018 | Casas |
| 10,159,530 B2 | 12/2018 | Lang |
| 10,194,131 B2 | 1/2019 | Casas |
| 10,278,777 B1 | 5/2019 | Lang |
| 10,292,768 B2 | 5/2019 | Lang |
| 10,326,975 B2 | 6/2019 | Casas |
| 10,368,947 B2 | 8/2019 | Lang |
| 10,405,927 B1 | 9/2019 | Lang |
| 10,511,822 B2 | 12/2019 | Lang |
| 10,594,998 B1 | 3/2020 | Casas |
| 10,602,114 B2 | 3/2020 | Casas |
| 10,603,113 B2 | 3/2020 | Lang |
| 10,646,285 B2 | 5/2020 | Siemionow et al. |
| 10,742,949 B2 | 8/2020 | Casas |
| 10,743,939 B1 | 8/2020 | Lang |
| 10,799,296 B2 | 10/2020 | Lang |
| 10,841,556 B2 | 11/2020 | Casas |
| 10,929,670 B1 | 2/2021 | Troy et al. |
| 2005/0215879 A1 | 9/2005 | Chuanggui |
| 2005/0251030 A1 | 11/2005 | Azar et al. |
| 2005/0259882 A1 | 11/2005 | Dewaele |
| 2005/0262031 A1 | 11/2005 | Saidi et al. |
| 2007/0060799 A1 | 3/2007 | Lyon et al. |
| 2007/0066881 A1 | 3/2007 | Edwards et al. |
| 2007/0090197 A1 | 4/2007 | Senda |
| 2007/0167735 A1 | 7/2007 | Zhong et al. |
| 2007/0228171 A1 | 10/2007 | Thiyagarajah |
| 2008/0208041 A1 | 8/2008 | Gilboa |
| 2008/0269664 A1 | 10/2008 | Trovato et al. |
| 2009/0078772 A1 | 3/2009 | Ofek et al. |
| 2010/0049548 A1 | 2/2010 | Kubota |
| 2010/0099980 A1* | 4/2010 | Godara ............... A61B 90/92 600/424 |
| 2011/0105895 A1 | 5/2011 | Kornblau et al. |
| 2011/0268248 A1* | 11/2011 | Simon .................. G16H 40/63 378/62 |
| 2011/0306986 A1 | 12/2011 | Lee et al. |
| 2012/0078236 A1 | 3/2012 | Schoepp |
| 2013/0345718 A1 | 12/2013 | Crawford et al. |
| 2014/0148818 A1 | 5/2014 | Komuro et al. |
| 2014/0160002 A1 | 6/2014 | Dent |
| 2014/0210856 A1 | 7/2014 | Finn et al. |
| 2014/0275760 A1 | 9/2014 | Lee et al. |
| 2014/0355840 A1 | 12/2014 | Pearson |
| 2015/0161802 A1 | 6/2015 | Christiansen |
| 2015/0173715 A1 | 6/2015 | Raghavan et al. |
| 2016/0035139 A1 | 2/2016 | Fuchs et al. |
| 2016/0143699 A1 | 5/2016 | Tanji |
| 2016/0180441 A1 | 6/2016 | Hasan et al. |
| 2016/0220393 A1 | 8/2016 | Slivka et al. |
| 2016/0249989 A1 | 9/2016 | Devam et al. |
| 2016/0270853 A1 | 9/2016 | Lavallee et al. |
| 2017/0045938 A1 | 2/2017 | Aoyama et al. |
| 2017/0116729 A1* | 4/2017 | Stolka ..................... G06T 7/11 |
| 2017/0178540 A1 | 6/2017 | Rios et al. |
| 2017/0296292 A1* | 10/2017 | Mahmood .............. A61B 90/14 |
| 2017/0368369 A1 | 12/2017 | Heinrich et al. |
| 2018/0064385 A1 | 3/2018 | Schwartz |
| 2018/0177403 A1 | 6/2018 | Kim-Whitty |
| 2018/0247128 A1* | 8/2018 | Alvi ....................... G16H 15/00 |
| 2019/0015009 A1 | 1/2019 | Dyer et al. |
| 2019/0053851 A1 | 2/2019 | Siemionow et al. |
| 2019/0142519 A1 | 5/2019 | Siemionow et al. |
| 2019/0365498 A1* | 12/2019 | Gibby ..................... G06F 3/012 |
| 2020/0145495 A1 | 5/2020 | Coffey et al. |
| 2020/0186786 A1 | 6/2020 | Gibby et al. |
| 2020/0188030 A1 | 6/2020 | Kopper et al. |
| 2020/0375666 A1 | 12/2020 | Murphy |

FOREIGN PATENT DOCUMENTS

| | | |
|---|---|---|
| WO | WO 2014200016 | 12/2014 |
| WO | WO 2016/162789 | 10/2016 |

OTHER PUBLICATIONS

Blackwell et al.; "An Image Overlay System for Medical Data Visualization;" Medical Image Computing and Computer-Assisted Intervention; (MICCAI 1998); First International Conference; (Oct. 1998); pp. 232-240; Cambridge, MA; <doi: 10.1007/BFb0056006>.

Sutherland et al. "Applying Modern Virtual and Augmented Reality Technologies to Medical Images and Models", Journal of Digital Imaging, Feb. 15, 2019, pp. 38-53. Retrieved on Jun. 17, 2021. Retrieved from URL: https://pubmed.ncbi.nlm.nih.gov/30215180/.

"QR code tracking," Microsoft Hololens Documentation, obtained at https://docs.microsoft.com/en-us/windows/mixed-reality/qr-code-tracking, Oct. 18, 2021.

Microsoft Hololens for Developers, Full Document, Microsoft Hololens Documentation, obtained at https://docs.microsoft.com/en-us/windows/mixed-reality/qr-code-tracking, Oct. 18, 2021.

* cited by examiner

USING OPTICAL CODES WITH AUGMENTED REALITY DISPLAYS

BACKGROUND

Mixed or augmented reality is an area of computing technology where images from the physical world and virtual computing worlds may be combined into a mixed reality world. In mixed reality, people, places, and objects from the physical world and virtual worlds become a blended environment. A mixed reality experience may be provided through existing commercial or custom software along with the use of VR (virtual reality) or AR (augmented reality) headsets.

Augmented reality (AR) is an example of mixed reality where a live direct view or an indirect view of a physical, real-world environment is augmented or supplemented by computer-generated sensory input such as sound, video, graphics or other data. Augmentation is performed as a real-world location is viewed and in context with environmental elements. With the help of advanced AR technology (e.g. adding computer vision and object recognition) the information about the surrounding real world of the user becomes interactive and may be digitally modified.

An issue faced by AR systems or AR headsets is identifying a position and orientation of an object with a high degree of precision. Similarly aligning the position of a virtual element with a live view of a real-world environment may be challenging. The alignment resolution of an AR headset may be able to align a virtual object to a physical object being viewed but the alignment resolution may only be aligned to within a few centimeters. Providing alignment to within a few centimeters may be useful for entertainment and less demanding applications but greater positioning and alignment resolution for AR systems may be desired in the scientific, engineering and medical disciplines. As a result, positioning and alignment processes may be done manually which can be time consuming, cumbersome, and inaccurate.

DETAILED DESCRIPTION

Figure 1:
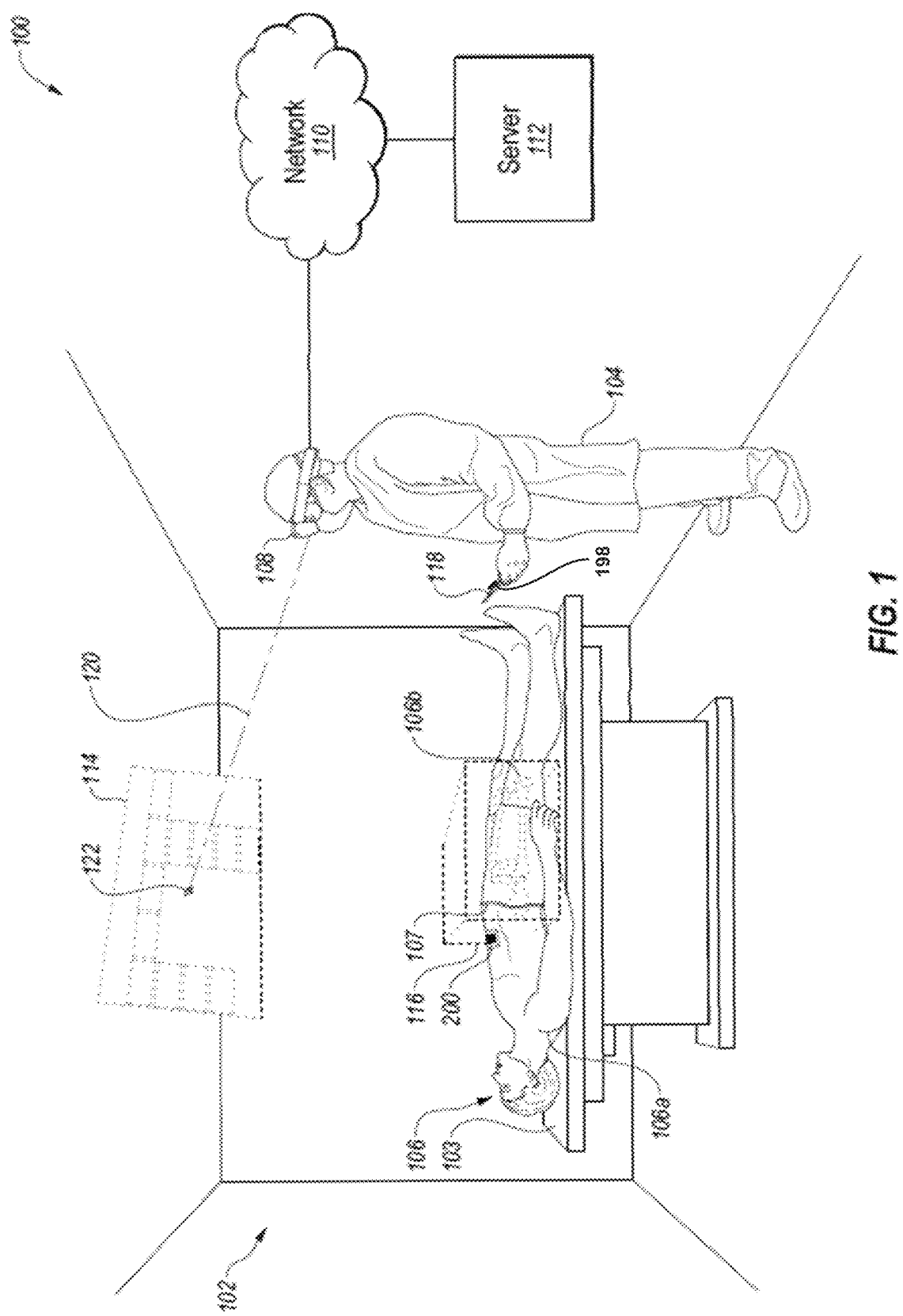
FIG. 1 illustrates an example augmented reality (AR) environment in which a medical implement and image data of a patient may be referenced and aligned to actual views of the patient using one or more optical codes attached to the patient and the medical implement.

A technology is provided for using an augmented reality (AR) headset to enable one or more optical codes to be identified on a medical implement that is in view of a camera of the AR headset during a medical procedure. The medical implement can be referenced to an image data set that is aligned with a body of a person using one or more optical codes and image visible markers on the body of the person. The image data set may be a previously acquired image of a portion of body of a person using a non-optical imaging modality (e.g., using MRI (magnetic resonance imaging), CT (computed tomography) scanning, X-ray, etc.). The image data set can be aligned to the body of the person using an image visible marker that is a fixed distance from at least one optical code located on the body of the person. For example, an image visible marker and an optical code (e.g., an AprilTag or 2D optical bar code) may both be attached onto one piece of material (e.g., co-located or in fixed proximity of each other) to facilitate the alignment of the image data set with the body of the person. An image visible marker is a marker that can be viewed in a non-visible imaging modality, such as a captured radiology image or an image data set, which may not be optically visible to the AR headset. The image data set may be captured with a representation of the image visible marker using machine captured images that capture structures of the human body with a non-optical imaging modality. The representation of the image visible marker in the image data set may be aligned with the body of the patient using the known fixed position of the image visible marker with respect to the one or more optical codes affixed on the body of the person (as described in further detail later). For example, the image visible marker may be a radiopaque marker, an MRI bead, an echogenic structure for ultrasound, etc.

Referencing the medical implement to the image data set may also include identifying a position and orientation of the medical implement with respect to the body of the person and the image data set. Accordingly, a medical professional to view a virtual interior of the patient using the image data set as referenced to a medical implement using an optical code on the medical implement, while looking at the actual patient through an AR headset. Visual image data that includes the medical implement may be captured using a visible light camera of the AR headset. One or more optical codes that are visibly displayed on the medical implement may also be scanned. For example, the position and orientation of the medical implement may be determined by scanning the one or more optical codes (e.g., an APRIL code or a 2D (two dimensional) bar code). The medical implement may be a medical instrument, a trocar, a catheter, orthopedic hardware, a surgical implant, a clamp, an electrocautery blade or system, an operating room object, an equipment object, a therapy object, a medical procedure object, a therapeutic object, an insertable implement, an implantable object, a medical device, etc.

A visual indicator, annotations, or a virtual tool may be integrated into the image data set can be provided to guide positioning and orientation of the medical implement with respect to the body of a patient and the image data set using the AR headset. The medical implement or virtual tool may also have a graphical indicator (e.g., computer generated graphics or symbols) displayed in proximity to or as an overlay to the medical implement or virtual tool using the AR headset to highlight the medical implement or virtual tool, or the graphical indicator may represent whether the medical implement is associated with the medical procedure. Medical information can also be retrieved that is instructional information describing the use of the medical implement in a medical procedure. In addition, the contours or outline of the medical implement may be detected using the one or more optical codes on the medical implement as a starting point. The use of automatic detection and alignment may avoid or reduce time consuming and cumbersome manual alignment of the medical implement and image data set with actual views of the patient.

In another configuration of the technology, an augmented reality (AR) headset or an AR display can align and display a fluoroscopic image and an image projection from an image data set with respect to a body of a person. A position and orientation of the fluoroscopic image as an image projection may be defined by a position and orientation of a fluoroscopic device which is mobile with respect to the body of the person. In this context, the description of an imaging device, which is mobile with respect to the body of the person, includes imaging device mobility where the imaging device may change the imaging device's orientation or move emitters, detectors, transducers, and/or imaging components of the imaging device with respect to the body of the person. The one or more optical codes on the fluoroscopic device can be used to determine the position and orientation of the fluoroscopic device with respect to the body of the person or patient. The fluoroscopic image and the image projection may be displayed with the portion of the body of the person being fluoroscopically imaged. This alignment and display can use one or more optical codes and image visible markers on the body of the person and one or more optical codes on the fluoroscopic device. Optical codes on the body of the person and the optical codes on the fluoroscopic device can be identified in visual image data captured by a camera of an AR headset.

At least one of the optical codes on the body of the person can have a fixed position relative to an image visible marker. This allows an image data set (e.g., a radiology image) to be aligned to the body of the person using a fixed distance between the image visible marker and the one or more optical codes on the body of the person, as viewed through an AR display (e.g., an AR headset). An image projection may be created from the image data set based on the position and orientation of the fluoroscopic device. A fluoroscopic image from the fluoroscopic device may be aligned with the body of the person and the image projection based on the image visible marker (e.g., a radiopaque object) and/or the one or more optical codes defining the position and orientation of the fluoroscopic device. Further, the fluoroscopic image may be virtually displayed in an AR headset in a location with respect to a body of a person where the X-ray beam is passing through the body of the person and the fluoroscopic image may be aligned to overlay the portion of the body of the person being imaged with the X-ray beam. The image projection may be oriented parallel to the fluoroscopic image and may be displayed in the AR headset as virtually being in at least part of a path of an X-ray beam. The aligned images may be displayed using the AR headset along with the real world or real view of the patient or the aligned images may be displayed on a separate AR display (e.g., a separate display screen). This process allows live fluoroscopic images, image data sets (e.g., augmented reality image or the image projection), and an actual view of a person to be combined, positioned, and oriented so that useful aspects of the fluoroscopic images (e.g., guiding of radiopaque object within a body of a person) and the image data set (e.g., better tissue contrast, etc.) are combined during a medical procedure.

In another configuration using fluoroscopic images, a change in the position and orientation of a fluoroscopic device can be detected with respect to the body of the person using one or more optical codes on the fluoroscopic device. Then the image projection and fluoroscopic image position and orientation may be modified as defined by the change in position and orientation of the fluoroscopic device. For example, movement of the projection of the image data set may be co-localized or synchronized to match the fluoroscopic image based on a change in orientation and position of the fluoroscope device. The zooming of the fluoroscopic device may also be detected using a radiopaque object on a body of a person, and the size of the radiopaque object may be used to adjust a size of the image projection as viewed on an AR display. Graphical indicators, virtual tools, or a virtual targeting system may also be included on the image data set and co-localized to the fluoroscopic image to guide the positioning and orientation of a fluoroscopically visible object (e.g., a trocar or needle) with respect to the body of the person and the image data set using the AR display.

In another configuration, the optical codes detected or captured by a camera or an AR headset may be used to confirm that the correct medical procedure is being performed on the correct patient. In addition, information related to the person or patient in the medical procedure may also retrieved using the optical codes and may be displayed to medical personnel using an AR system. The optical codes may also assist in confirming the identity of the patient. A confirmation may also be performed to determine that a correct portion of the body and a correct medical implement are in the medical procedure using one or more optical codes on the body and the medical implement.

FIG. 1 illustrates an example augmented reality (AR) environment 100 in which an image data set of a patient 106 or person may be aligned with actual views of the patient 106 using an optical code 200 affixed to the patient 106. The environment 100 may include a physical space 102 (e.g., operating theater, a lab, etc.), a user 104, the patient 106, multiple optical codes 200 on the patient, a medical implement 118 with an optical code 198, and an AR headset 108 in communication with a server 112 over a computer network 110. A virtual user interface 114 and a virtual cursor 122 are also shown in dashed lines to indicate that these virtual elements are generated by the AR headset 108 and are viewable by the user 104 through the AR headset 108.

The AR headset 108 may be an AR computing system that is capable of augmenting actual views of the patient 106 with an image data set. For example, the AR headset 108 may be employed by the user 104 in order to augment actual views of the patient 106 with one or more 3D image data set views or radiologic images of the patient 106 including, but not limited to, bones 106b (as illustrated in FIG. 1), muscles, organs, or fluids. The AR headset 108 may allow an image data set (or a projection of the image data set) to be dynamically reconstructed. So, as the user 104 moves around the patient 106, the sensors of the AR headset 108 determine the location of the user 104 relative to the patient 106, and the internal anatomy of the patient displayed using the image data set can be reconstructed dynamically as the user chooses different orientations relative to the patient. For example, the user 104 may walk around the patient 106. Then the AR headset 108 may augment actual views of the patient 106 with one or more acquired radiology images or image data sets (MRI, CT scan, etc.) of the patient 106, so that both the patient 106 and the image data set of the patient 106 may be viewed by the user 104 from any angle (e.g., a projected image or a slice from the image data set may also be displayed). The AR headset 108 may be a modified version of the Microsoft HOLOLENS, Meta Company META 2, Epson MOVERIO, Garmin VARIA VISION or other AR headsets.

The optical code(s) 200 may be affixed to the patient 106 prior to the generation of image data of the patient 106 (e.g., capture of the MRI, CT scan, X-ray, etc.), and then remain affixed to the patient 106 while the patient 106 is being viewed by user 104 through the AR headset 108. Then, the optical code 200 and image visible marker may be employed by the AR headset 108 to automatically align the image data set of the patient 106 with actual views of the patient 106. Further, employing the same optical code 200 used during the capturing of the image data to automatically retrieve the image data may ensure that the image data retrieved by the AR headset 108 matches the actual patient 106 being viewed through the AR headset 108.

The AR headset 108 has sensor technology that may map or detect the surface of the patient and similarly can map the surface of the medical implement 118, and this detected surface mapping data may be co-registered to the image data set. The medical implement 118 may be frequently moved in the environment 100, and the real-time position of the medical implement 118 may be tracked in the 3D space 102 using the optical code and the medical implement 118 may be referenced to the image data set 116 or a body of the patient 106. When the user 104 inserts some portion of the medical implement 118 into the body of the patient 106, the AR headset 108 may display a virtual inserted portion of the medical implement 118 projected into the image data set 116 to depict the medical implement 118 in the inner anatomy of the patient 106. In this manner, the virtual inserted portion of the medical implement 118 may be projected onto actual views of the user 104 and referenced to the image data set even when the actual inserted portion of the medical implement 118 is hidden from the actual views of the user 104. The medical implement 118 may be tracked using one or more optical codes affixed to the medical implement 118, and then the one or more optical codes can be detected by the AR headset to establish a continually updating position of the medical implement 118 with reference to the image data set 116 and the body of the person or patient 106. In some embodiments, the medical implement 118 may be anything that the user 104 wishes to insert into the patient 106. For example, the medical implement 118 may include, but is not limited to, a needle, a trocar, a scalpel (as illustrated in FIG. 1), a scope, a drill, a probe, a clamp, an implant, another medical instrument.

A virtual user interface 114 may be generated by the AR headset 108 and may include options for altering the display of the projected inner anatomy of the patient 106 from the image data set 116 of the patient 106. The virtual user interface 114 may include other information that may be useful to the user 104. For example, the virtual user interface 114 may include information about the patient or the medical implements 118 (e.g., medical instruments, implants, etc.) being identified with an optical code. In another example, the virtual user interface 114 may include medical charts or other medical data of the patient 106. In some configurations, the image data 116 or captured radiological data of a person may be displayed by the AR headset 108 using a volume of the image data 116 to display radiologically captured anatomy (e.g., bones 106b, tissue, vessels, fluids, etc.) of the patient 106 from the image data. This image data may contain axial slices, coronal slices, sagittal slices, or oblique slices of the image data. Slices may be two-dimensional (2D) slices, three-dimensional (3D) slices, and/or four dimensional (4D) slices (3D images with a time sequence of images) that have a depth as well as a height and width (e.g., one or more layers of voxels). A user 104 may control the virtual user interface 114 using: hand gestures, voice commands, eye movements, remote controls (e.g., a finger clicker), a 3D mouse, a VR wand, finger sensors, haptic technology, or other control methods.

In one example configuration, multiple users each wearing an AR headset 108 may be simultaneously present to view the patient 106 augmented with image data of the patient 106. For example, there may be multiple AR headsets 108 that are used during medical procedures. One AR headset 108 may be used by a first medical professional to adjust and manipulate the radiological images being displayed to both AR headsets and the second head set may be used by a second medical professional to assist in performing the medical procedure on the patient. Additionally, one medical professional may be able to turn on or off the radiological image at the request of the other medical professional.

Figure 2:
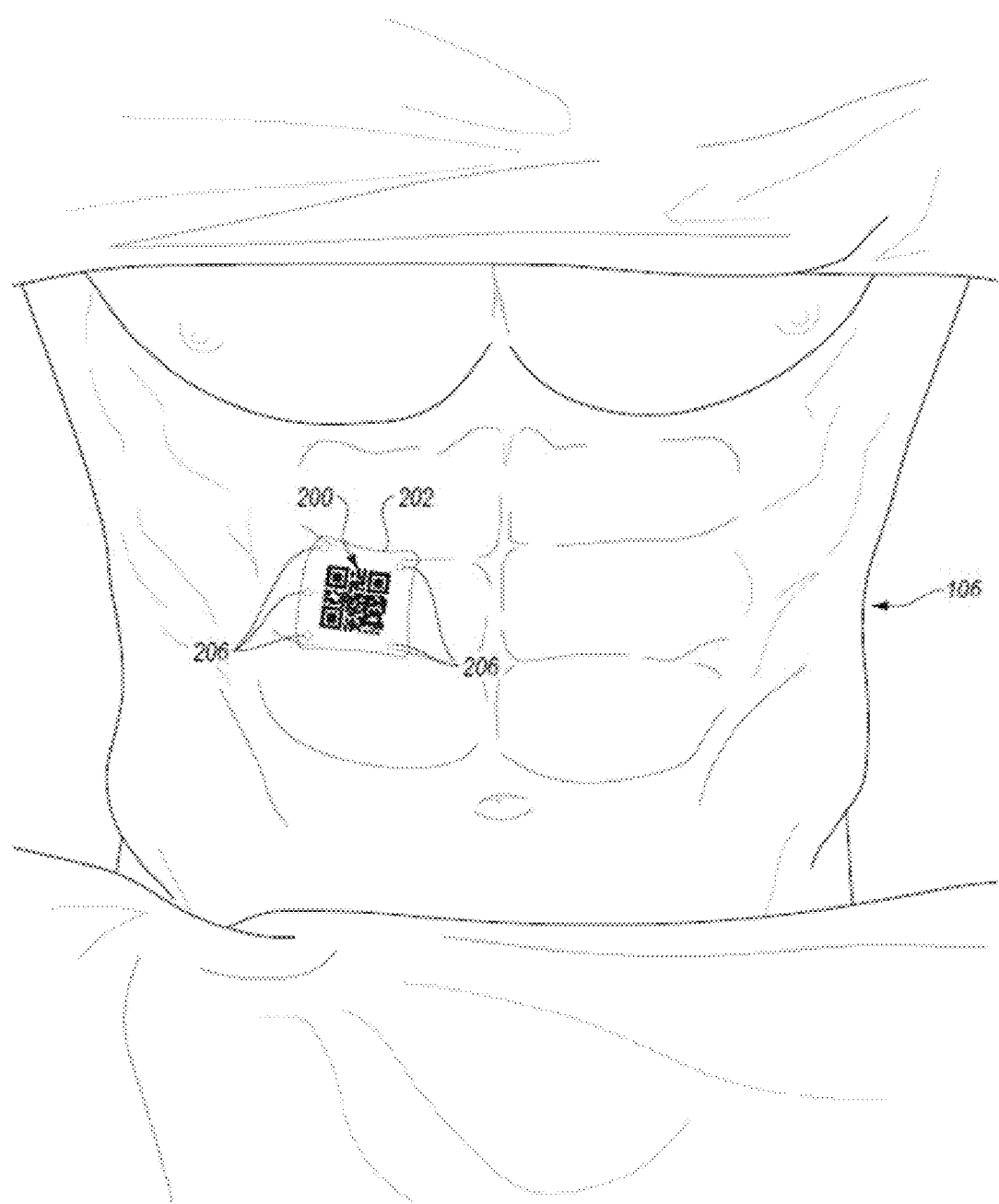
FIG. 2 illustrates an example of the optical code with an image visible marker that is affixed to a patient.

FIG. 2 illustrates the optical code 200 of FIG. 1 affixed to the patient 106 of FIG. 1. With reference to both FIG. 1 and FIG. 2, the optical code 200 may be perceptible to an optical sensor, such as an optical sensor built into the AR headset 108. In some embodiments, the optical code 200 may be an AprilTag, a linear barcode, a matrix two-dimensional (2D) barcode, a Quick Response (QR) code, or some combination thereof. An AprilTag is type of two-dimensional bar code which may be a visual fiducial system which is useful for augmented reality and camera calibration. The AprilTags may be used to compute the 3D position, orientation, and identity of the tags relative to a camera, sensor, or AR headset.

The optical code 200 may be linked to medical data of the patient 106 such that the medical data of the patient 106 can be accessed with the optical code 200. For example, the optical code 200 may be used to automatically retrieve the image data set to be used in a medical procedure for the patient using the AR system.

The optical code 200 may further be associated with markers 206 or image visible markers that are perceptible to a non-optical imaging modality. Examples of a non-optical imaging modality may include, but are not limited to, an MRI modality, a Computerized Tomography (CT) scan modality, an X-ray modality, a Positron Emission Tomography (PET) modality, an ultrasound modality, a fluorescence modality, an Infrared Thermography (IRT) modality, 3D Mammography, or a Single-Photon Emission Computed Tomography (SPECT) scan modality. In another example, the non-optical images or image data sets may be an image or image data set which includes a combination of two or more forms of non-optical imaging modality as listed above (e.g., two or more images combined together, combined segments of two or more non-optical images, a CT image fused with an MRI image, etc.). Each image data set in a separate modality may have an image visible code in the individual image data set which may allow a PET image, a CT image, an MRI image, a fluoroscopy image, etc., to be aligned and referenced together with an optical code on a body of a person in an AR system view. Forming the markers 206 from a material that is perceptible to a non-optical imaging modality may enable the markers 206 or image visible markers to appear in an image data set of the patient 106 that is captured using a non-optical imaging modality. Examples of markers 206 include, but are not limited to: metal spheres, liquid spheres, radiopaque plastic, metal impregnated rubber, metal strips, paramagnetic material, and sections of metallic ink.

The markers 206 or image visible markers may be arranged in a pattern and may have a fixed position relative to a position of the optical code 200. For example, in the embodiment disclosed in FIG. 2, the optical code 200 may be printed on a material 202 (such as an adhesive bandage, paper, plastic, metal foil, etc.) and the markers 206 may be affixed to the material 202 (e.g., embedded in the material 202 and not visible on any surface of the bandage). In this embodiment, the markers 206 may be arranged in a pattern that has a fixed position relative to a position of the optical code 200 by being arranged in the fixed pattern in the bandage 202. Alternatively, the markers 206 may be embedded within the optical code 200 itself, such as where the markers 206 are embedded within an ink with which at least some portion the optical code 200 is printed on the material 202 and the ink includes a material that is perceptible to the non-optical imaging modality, such as ink particles that are radiopaque and are not transparent to X-rays. In these embodiments, the optical code 200 itself may serve both as an optical code and as the pattern of markers. Additionally, the markers 206 may be arranged by affixing or printing (at least temporarily) the optical code 200 directly on the skin 106a of the patient 106. By arranging the markers 206 in a pattern that has a fixed position relative to a position of the optical code 200, this fixed position may be employed to calculate the location of the pattern of the markers 206 or image visible markers with respect to a visible location of the optical code 200, even where the markers 206 are not themselves visible or perceptible to sensors of the AR headset 108.

Once the optical code 200 and the markers 206 are affixed to the patient 106 in a fixed pattern, the non-optical imaging modality (to which the markers 206 are perceptible) may be employed to capture image data of the patient 106 and of the markers 206. In particular, the image data may include internal anatomy (such as bones 106b, muscles, organs, or fluids) of the patient 106, as well as including the pattern of markers 206 in a fixed position relative to the positions of the inner anatomy of the patient 106. In other words, not only will the internal anatomy of the patient 106 appear in the image data of the patient 106, but the markers 206 will also appear in the image data set of the patient 106 in a fixed pattern, and the position of this fixed pattern of the markers 206 will appear in the image data set in a fixed position relative to the positions of the internal anatomy of the patient 106. In one example, where the non-optical imaging modality is a CT scan modality, the CT scan images may display the bones 106b, organs, and soft tissues of the patient 106, as well as the markers 206 arranged in a fixed position with respect to the positions of the bones 106b, organs, and soft tissues of the patient 106.

Further, the patient 106 may be moved, for example, from a medical imaging room in a hospital to an operating room in the hospital. Then a user 104 (such as a medical professional) may employ the AR headset 108 to determine a location of the optical code 200 on the body of a person or patient. Next, the AR headset 108 may automatically retrieve the image data of the patient 106 based on the optical code.

After detecting the optical code 200 in the 3D space 102, the AR headset 108 may automatically calculate the position of the pattern of the markers 206 in the 3D space 102 and with respect to one another. This automatic calculation may be based on the sensed position of the optical code 200 in the 3D space 102 and may also be based on the known fixed position of the pattern of the markers 206 relative to the position of the optical code 200. Even where the markers 206 are not perceptible to the AR headset 108 (for example, due to the markers 206 being embedded or underneath a material), the AR headset 108 can automatically calculate the location of the pattern of the markers 206 based on the position of the optical code 200 and on the fixed position of the pattern of the markers 206 relative to the position of the optical code 200. In this example, these fixed positions may enable the AR headset 108 to automatically calculate the position of the pattern of the markers 206 in the 3D space 102 with respect to one another even where the AR headset 108 is not directly sensing the positions of the markers 206.

After calculating the location of the pattern of the markers 206 or image visible markers in the 3D space 102, the AR headset 108 may then register the position of the internal anatomy of the patient 106 in the 3D space 102 by aligning the calculated position of the pattern of the markers 206 in the 3D space 102 with the position of the pattern of the markers 206 in the image data set. The alignment may be performed based on the calculated position of the pattern of the markers 206 in the 3D space 102 and the fixed position of the image data set to the markers 206 relative to the positions of the internal anatomy of the patient 106. This alignment and registration may then enable the AR headset 108 to display in real-time the internal anatomy of the patient 106 from the image data projected onto actual views of the patient 106.

Thus, the optical code 200, and the associated pattern of the markers 206, may be employed by the AR headset 108 to automatically align the image data of the patient 106 with actual views of the patient 106. Further, one or more optical codes 200 (e.g., an AprilTag and 2D bar code or another combination of optical codes) may be employed to automatically retrieve the image data obtained during the capturing of the image data may ensure that the image data retrieved by the AR headset 108 matches the actual patient 106 being viewed through the AR headset 108.

In a further example, multiple optical codes 200 may be simultaneously affixed to the patient 106 in order to further ensure accurate alignment of image data of the patient 106 with actual views of the patient 106 in the 3D space 102. Also, the pattern of five markers 206 disclosed in FIG. 2 may be replaced with another pattern, such as a pattern of three markers or a pattern of seven markers and each optical code may have a different pattern. Further, since the markers 206 are affixed to an outside layer of the patient 106, the markers 206 may not all be in one plane, but instead may conform to any curvatures of the outside layer of the patient 106. In these embodiments, the fixed position of the pattern of the markers 206 relative to a position of the optical code 200 may be established after affixing the optical code 200 and the markers 206 to the patient 106 to account for any curvatures on the outside layer of the patient 106.

Figure 3:
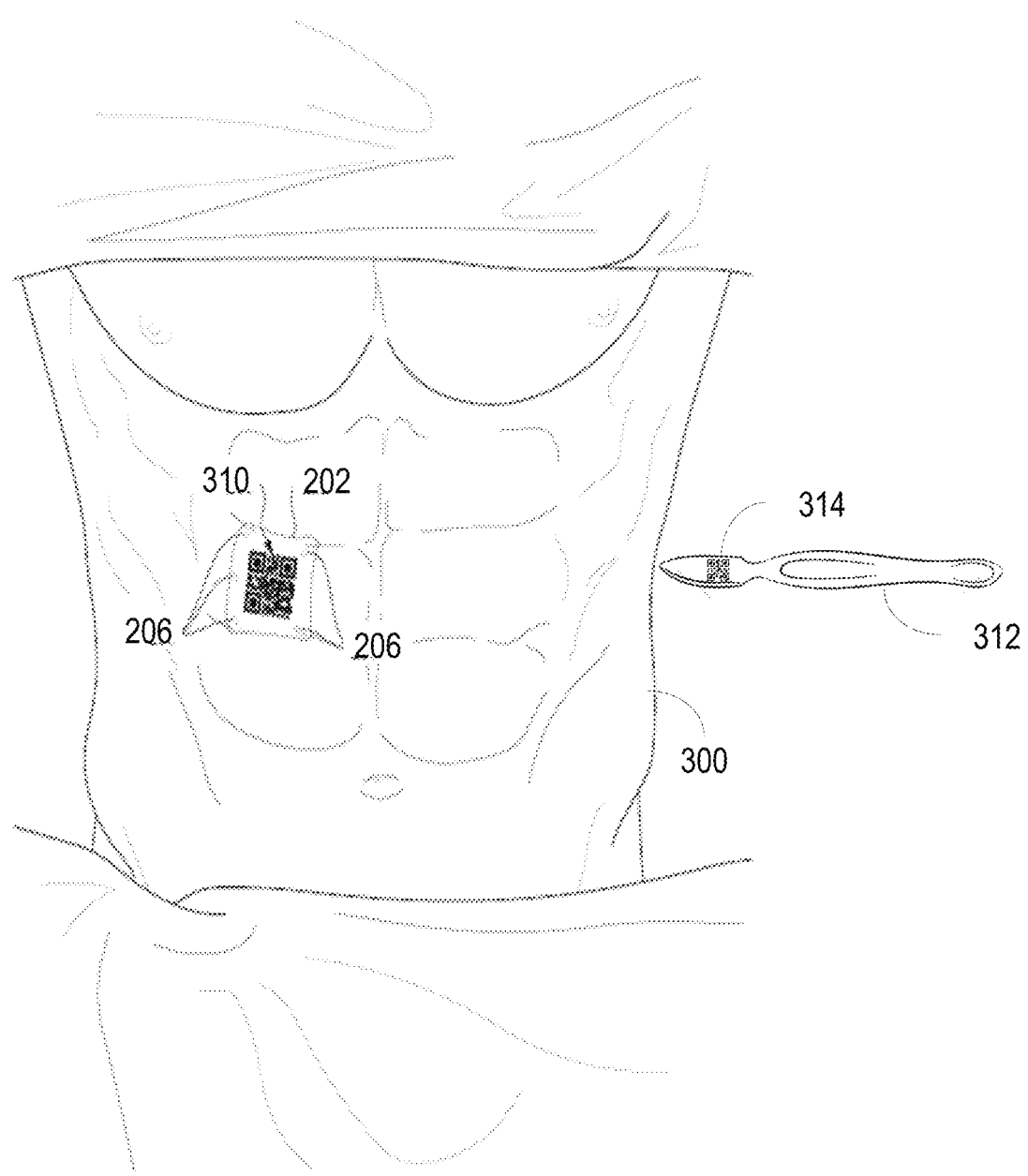
FIG. 3 illustrates an example of visual data that may be captured by a camera of an actual view a body of a patient and a medical implement and each have an optical code affixed.

FIG. 3 illustrates a visual image that may be captured by the camera of the AR headset or AR system. The visual image may include a body of a patient 300 and a medical implement 314, each with an optical code affixed. Optical codes may be used to identify the position and orientation of the medical implement 312 in the visual image and the optical code may be used as a starting point identify the contour or shape of the medical implement 312. In addition, the optical code 310 on the body of the person 300 may be used to access additional information for a patient (e.g., a patient record in a patient database) or a virtual object (e.g., in an object database) used as an overlay or as an additional virtual object for display.

In one configuration, multiple optical codes 314 may be used on the medical implement 312 to enable the position and orientation of the medical implement to be determined. For example, an optical code 314 may be affixed to multiple separate faces or surfaces of the medical implement. Each of these multiple optical codes may be coded to identify a specific face, aspect or orientation of the medical implement. The multiple optical codes may also be used in identifying a desired 3D (three dimensional) virtual image to associate with the medical implement. For example, highlight graphics or a virtual object (e.g., a virtual medical instrument) may be selected as an overlay for the medical implement.

Once the optical codes 310, 314 affixed to the patient 300 and the medical implement 314 have been used to identify a position and orientation of the body of the patient and medical implement 314 within the visual image, this position and orientation information can be tracked for each optical code and used when determining the position and orientation of the medical implements and patient in a procedure. The optical code 310 may be captured during the process of capturing a visual image of the patient during a procedure. As a result, the optical code 310 can be used to reference the medical implement 314 to the previously captured radiological images of the patient in an augmented reality display (e.g., such as in an AR headset).

Furthermore, the optical code 314 on the medical implement can be used to identify the particular type of medical implement 312 (e.g., a medical instrument or an orthopedic implant). Once the medical implement position and orientation is identified 314, the position of the medical implement can be determined relative to the image data set discussed above and the body of the patient. To better illustrate the position of the medical implement 314, the AR system may access information describing the medical implement's size, shape, and contours and well as any other relevant information.

In one example, additional information associated with the medical implement 312 may also be retrieved. For example, information concerning the use of a medical instrument may be retrieved and displayed in the AR headset. This may include information regarding how to best align the medical instrument with body of the patient, tips for inserting an implant into a bone, settings for an electronic medical sensor, or other guidance information for the medical implement.

In addition, the AR system may have records identifying which medical implements 312 are associated with a particular medical procedure. By using this information in combination with the optical codes, the augmented reality system may determine whether a particular medical implement 312 is correctly associated with or is correctly being used in the current medical procedure. For example, in a medical procedure in which a medical implement 312 is to be implanted in a patient, a data store associated with the augmented reality system may be accessed to ensure that the correct implant is being implanted in the patient and that the correct tools are being employed. This combination of optical codes, procedure data, and patient data may be used to check: whether a correct patient is being operated on, whether a correct body part is being operated on, whether an implant for the correct side of the body is being used or whether a correct implant size is being used. Use of the optical codes on the medical implements 312 prior to the procedure, may provide increased confidence that the correct medical implements 312 are in the operating theater. In another example, the AR system may display an optical indicator confirming that a given medical implement 312 is authorized in a procedure or alerting a user that an incorrect medical implement 312 or instrument is present.

Figure 4:
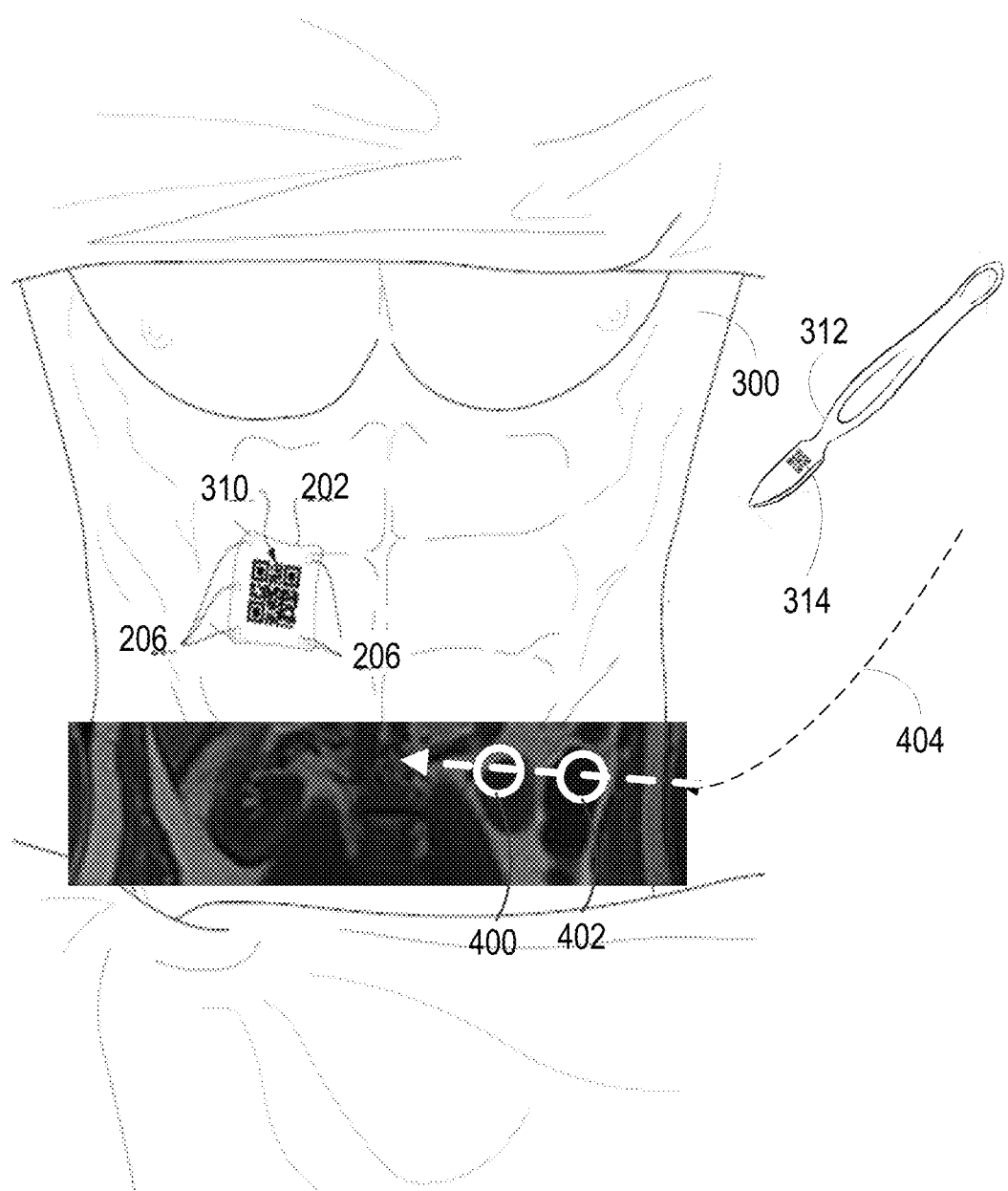
FIG. 4 illustrates an example of a view in an augmented reality (AR) display with annotations to guide positioning and orientation of a medical implement during a medical procedure.

FIG. 4 illustrates identifying additional information associated with a medical implement 312 during a medical procedure. As noted above, the AR system may use optical codes 314 to access information associated with the patient 300, the medical implement 312, and/or the medical procedure being performed. The AR system can display information associated with the use of a medical implement through an AR headset to aid a user during the procedure. In one example, this information may describe the proper use of the medical instrument. For example, if the AR system captures an optical code 314 on a medical instrumental 312, values in the optical code 314 can be used as a lookup value to retrieve information for that instrument from a database. Such information may further include planned medical procedure steps for use of the medical instrument 312 that can be displayed in the AR headset.

The medical professional may pre-plan certain aspects of a medical procedure. For example, the location and orientation of an incision or a path of cutting tissue may be pre-planned using annotations. These plans may be entered into a database associated with the augmented reality system. When desired, the user can instruct the augmented reality system to display the relevant pre-planned medical procedure information to the user in the AR headset. In this case, the user or system may have predetermined annotations 400, 402 to describe positioning of the medical instrument 612. A virtual guidance system may be displayed by the AR headset to illustrate a pre-planned path or an alignment point, line or plane for a medical instrument for a medical procedure. As a result, the augmented reality display may display a guidance annotation 404, along with an indication to move the medical implement 312 to the circle annotations 400, 402. When the medical professional has moved the medical instruments' position and orientation to the appropriate location and orientation (e.g., in three dimensions) as visually depicted using graphics in the AR headset, then graphical indicators, virtual tools, or a virtual targeting system may be displayed to show that the proper position and orientation have been satisfied. The positioning and orientation of the medical implement 312 may be guided in three dimensions or two dimensions. In one example, red indicators may be displayed when the medical instrument is not aligned, and when the medical instrument is aligned then green indicators may be displayed through the AR headset. Thus, annotations may be modified, animated and/or change color when a medical implement moves to defined positions, targets, entry points, or near target objects.

Similarly, a virtual implement or virtual tool may be displayed to allow alignment of a visible implement and virtual implement. For example, a graphical or virtual implement may be displayed or projected using an AR headset. When the visible implement or real world implement is aligned with the virtual implement or virtual tool, then the AR system can display a message or graphic indicating that the visible implement is aligned with the virtual implement. Further, this alignment of the virtual implement may also enable alignments with viewable anatomical structures in a previously acquired image data set or an image data set acquired during the procedure (e.g., CT scans or MIll images obtained during the procedure).

Figure 5:
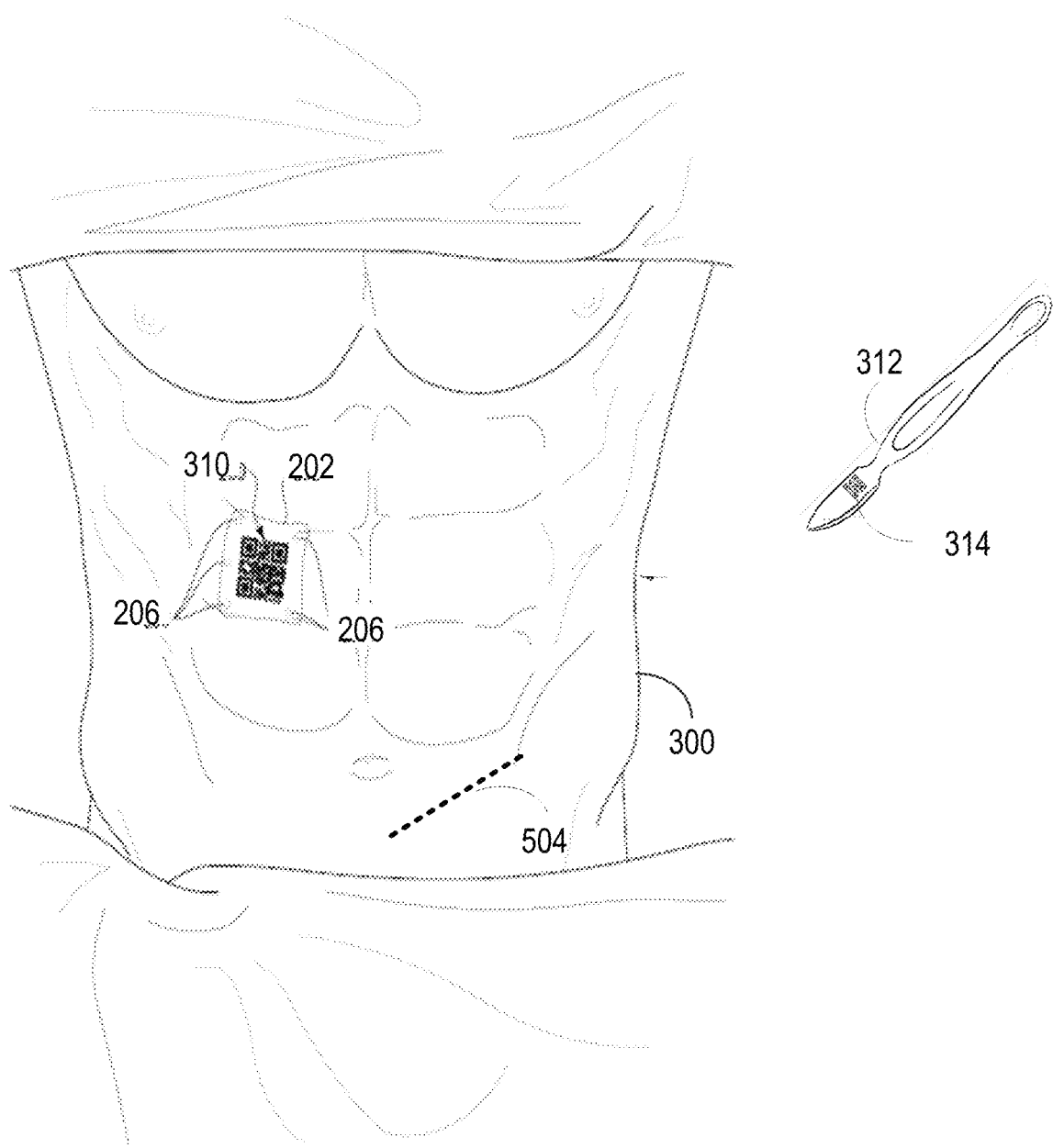
FIG. 5 illustrates example of a view that may be displayed in an augmented reality display device to display use or guidance information for a medical implement during a medical procedure.

FIG. 5 illustrates an incision point 504 is displayed in the AR display as an overlay or virtual object on a specific part of the patient's body. The user can the use this virtual incision point to guide the initial placement of the medical instrument with respect to the body of the person 300 and/or an image data set when beginning a surgery. Similarly, the ability to detect the position and orientation of the medical instrument may also include the ability to assist the medical professional by guiding the depth or angle of an incision, proper placement of clamps, and so on. In addition, the system may display instructions for a correct angle or orientation to hold a given medical implement. For example, the AR display can present graphical indicators, virtual tools, or a virtual targeting system in the AR display for correct movement of the instrument in a current medical procedure based on the position and orientation of the portion of the body of the patient. For example, the system may display a visual indication of a line, along which an incision is to be made that is customized to an individual body of a person. Similarly, the system can estimate a current depth of an instrument and indicate that the medical instrument is to be moved with respect to the body of a patient and/or an image data set. During the procedure, the augmented reality system can use one or more optical codes (e.g., either the optical codes on the patient 310 or the medical implement 312) to access, align and display the planning information in the AR display to guide the medical professional.

In a medical preparation configuration, the use of the optical codes, as described in this disclosure, may enable a medical professional who is preparing a patient for a medical procedure to be graphically instructed to identify a portion of a patient's body or anatomy where the skin should be prepped or other medical preparations should be made before a medical procedure. For example, after the AR headset has identified one or more optical codes on patient's body, then graphical lines, graphical shapes or virtual tools may be displayed in the AR headset to assist the medical professional performing medical preparation. This can guide the medical professional to position, orient, and prepare the patient in the correct anatomical location, prepare the correct incision point, and/or prepare on the correct portion of the patient's anatomy. For example, it may be difficult to locate the correct vertebrae or hip location on a patient, and this technology provides such guidance. This guidance may improve the overall throughput in a surgical theater and for surgical technicians.

Figure 6:
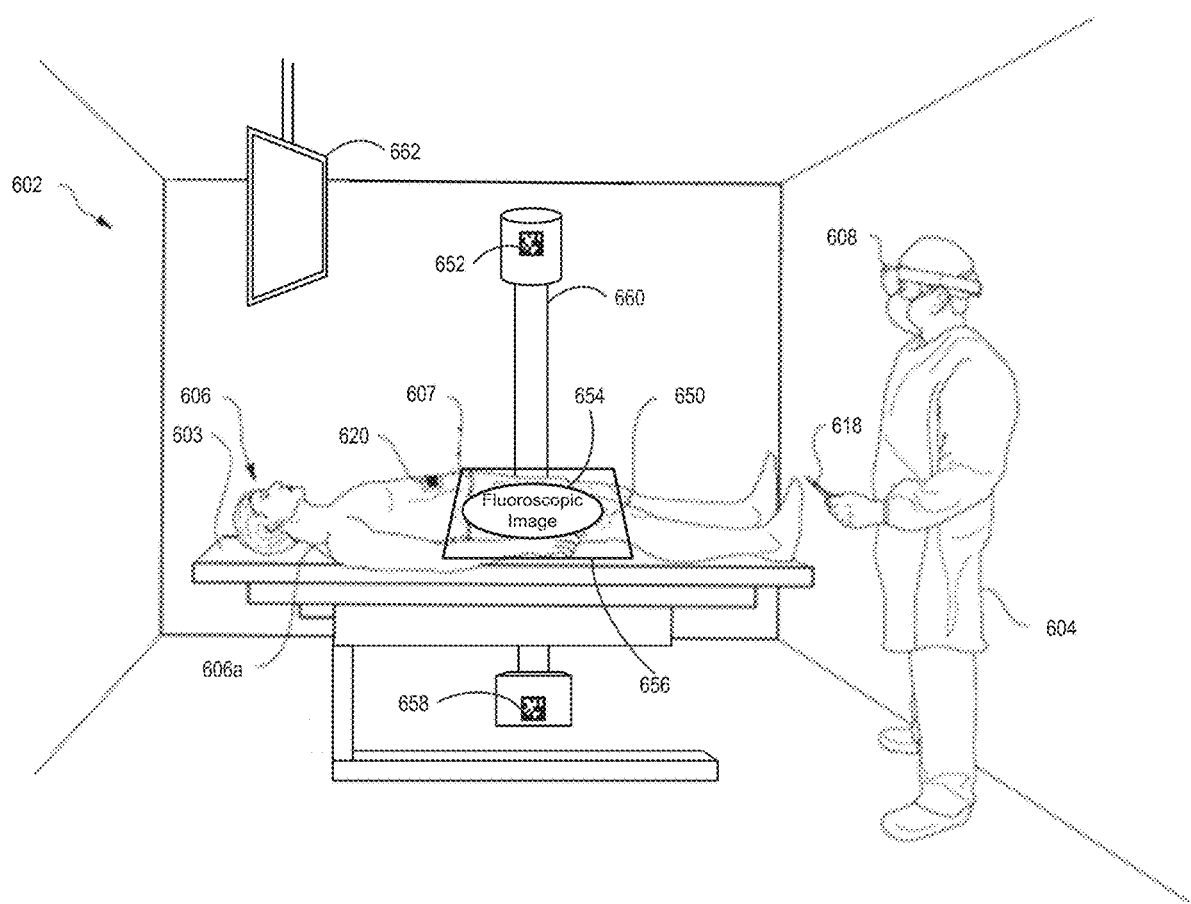
FIG. 6 illustrates an example of using an augmented reality (AR) display to enable positioning and orientation of a fluoroscopic image and an image projection from an image data set with respect to a body of a person using optical codes.

FIG. 6 illustrates a technology 602 for using an augmented reality (AR) system to display a fluoroscopic image 654 and an image projection 656 from an image data set, as aligned with respect to a body of a person 606a. A fluoroscopic device 660 may send a beam of X-rays (e.g., continuous X-rays) through the patient to obtain a series of fluoroscopic images or live video of the fluoroscopic imaging of the patient viewable by the medical professional. The fluoroscopic device 660 may also be mobile with respect to the body of the person. The fluoroscopic image 654 and image projection 656a may have position and/or orientation defined by a fluoroscopic device 660 and/or an image visible marker. A camera or optical sensor (e.g., a visible light sensor or IR sensor) linked to the AR system or AR headset 608 may capture visual image data of a portion of a body of a person on an operating table 603 and a fluoroscopic device 660 which is mobile with respect to the body of the person. One or more optical codes on the body of the person 606a and one or more optical codes on the fluoroscopic device 652, 658, can be identified and scanned in from the visual image data using optical code recognition and scanning techniques or other optical code recognition techniques.

An image projection 656 may be selected to display a portion an image data set that is associated with (e.g., parallel to, oblique to, or another fixed orientation) a fluoroscopic image 654 is being captured. The image projection may also display a specific anatomy type for the body of the person, such as veins, nerves or bones. The fluoroscopic image 654 may be a single layer projection (e.g., a two-dimensional (2D) projection). Alignment, positioning and orientation may be performed using: optical codes 620 and image visible markers on the body of the person, representations of image visible markers on the image projection, image visible markers captured in the fluoroscopic image 654, and optical codes 652, 658 on the fluoroscopic device (e.g., a C-arm device, a catheterization lab, an angiographic lab, or a fluoroscopic device with a movable emitter and detector).

At least one of the optical codes 620 on the body of the person can have a fixed position relative to an image visible marker (as described in detail previously). This allows an image data set (e.g., a captured radiology image) to be aligned with the body of the person 606 using the fixed position of the image visible marker with reference to the one or more optical codes on the body of the person. The body of the person may be covered with fabric 607 but the internal anatomy 650 of the body may be virtually viewed using the image data set.

An image projection 656 may be created from the image data set based on the position and orientation of the fluoroscopic device 660. The image projection 656 may be a coronal projection, an oblique projection or another projection orientation that matches the orientation of the fluoroscopic device 660. The image projection is projected from the image data set to define a single plane view or a "slab" that is a multi-planar reconstruction (MPR) of the image data set (e.g., multiple layer projection). The image projection may be of any selected thickness and may be a MIP (maximum intensity projection) of tissue in the appropriate view.

A position and orientation of the fluoroscopic device 660 with respect to the body of the person 606a can be determined using one or more optical codes 652, 658 on the fluoroscopic device 660. A fluoroscopic image 654 from the fluoroscopic device 660 may be aligned with the body of the person and the image data set based on the image visible marker and/or the optical codes on a body of the person 606a. Further, the fluoroscopic image 654 may be positioned and oriented using the position and orientation of the fluoroscopic device 660 with respect to the body of the person 606.

A radiopaque marker may be used as the image visible marker to line up the fluoroscopic image 654 with the body of the patient 606a. In some situations, the radiopaque marker may be the same image visible marker used for aligning the image data set or the radiopaque marker may be a completely separate radiopaque marker (e.g., a lead rectangle) that may have a separate optical codes. For example, the radiopaque marker may a first type of imaging modality marker used align the fluoroscopic image 654 with a body of a person while a second imaging modality marker (e.g., a MRI type marker or an ultrasonic marker) may be used to align an image data set with a body of a person. The aligned data set image, image projection, and fluoroscopic images may also be displayed using the AR headset 608 or on a separate AR display 662 along with the real world view of the patient. Thus, the augmented reality images may be combined into the live fluoroscopic interventional or diagnostic procedure performed on a body of a person 606a.

Multiple useful views can be provided to a medical professional who is using a fluoroscopic device and an AR system, as described earlier. One view may include the ability to take a partially transparent fluoroscopic image and overlay the fluoroscopic image so that the fluoroscopic image is anatomically aligned over the actual view of the patient using the optical codes. Another view may enable an image data set to be merged with the fluoroscopic image and be aligned with the patient's body using the optical codes. Additionally, a projection from the image data set may move or be reconstructed in concert with the medical professional's changing actual view of the body through the AR system or AR headset. Yet another view may be provided in an AR system that displays a combined view of the fluoroscopic image and a projection of the image data set (e.g., a 2D rectangular slice) that is parallel to the fluoroscopic image as aligned with and overlaid on the patient (e.g., what the medical professional would see if the medical professional were at the same perspective as the X-ray beam itself). In this configuration, the projection may move or be reconstructed as the fluoroscopic device moves.

A medical implement 618 with an optical code may also be referenced with respect to the image data set and image projection 656, as described earlier. This may enable a medical professional to view the medical implement 618 with reference to the image data set or image projection 656 and a fluoroscopic image 654 simultaneously. The fluoroscopic image 654 may be set to any level of transparency desired by the medical professional or user.

Figure 7:
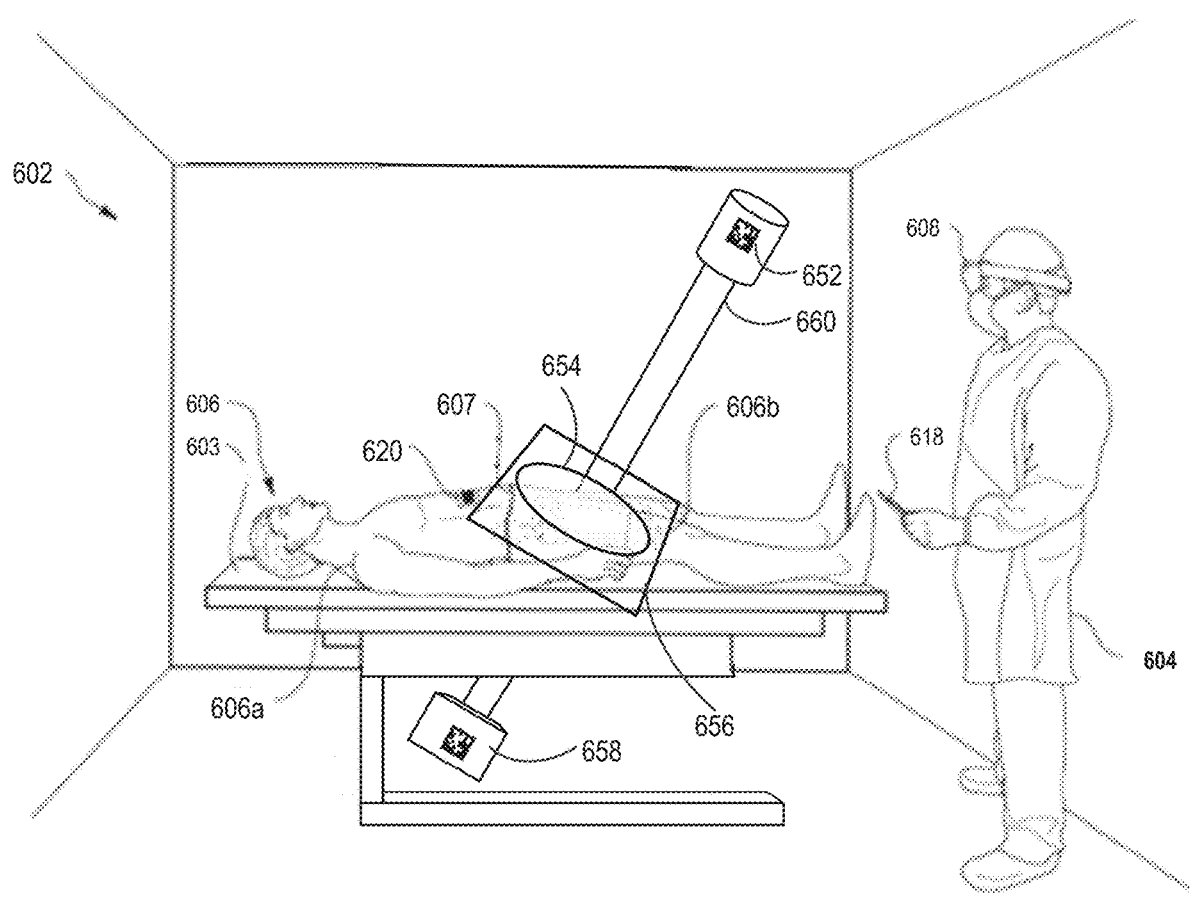
FIG. 7 illustrates an example of a fluoroscopic device which is mobile with respect to the body of the person and the fluoroscopic image and image projection are also moved and/or modified.

FIG. 7 illustrates that a position of a fluoroscopic device 660 may change with respect to a body 606a of a person or a patient to enable a medical professional 604 to obtain a fluoroscopic image 654 from a different perspective. The change in the position and orientation of a fluoroscopic device with respect to the body of the person can be detected and quantified using one or more optical codes 652, 658 captured by a camera associated with an AR headset 608 or AR system. Due to the change in position and orientation of the fluoroscopic device 660, the position and orientation of the image projection 656 and fluoroscopic image 654 may be modified. For example, the position and/or orientation of the image projection 656 may be moved, as viewed by the AR headset, based on detected changes in position and orientation of the fluoroscopic device 660 using the one or more optical codes 652, 658 as compared to the body of a patient 606a. The image projection 656 from the image data set may be reconstructed or a new projection may be created using the modified position and orientation of the fluoroscopic device 660.

For example, the fluoroscopic device 660 may rotate 45 degrees in one axis. As a result, the image projection 656 may be recreated at that new orientation and the fluoroscopic image 654 may be displayed at the rotated orientation, as viewed in the AR display, to enable the orientation of the fluoroscopic image 654 and the image projection 656 to be aligned in the appropriate orientation with respect to the body of the person 606a as viewed through AR headset. The fluoroscopic image 654 may have a modified orientation in 3D space with respect to the body of the person as defined by the optical codes on the body, image visible marker, and/or as defined by the modified position and/or orientation of the fluoroscopic device 660. Thus, position and orientation of the image projection 656 and fluoroscopic image 654 changes when the position and orientation of the X-ray beam changes.

Determining the position and orientation of the fluoroscopic device 660 relative to the patient, also enables the AR system to reconstruct the image projection so the image projection 656 is parallel to the fluoroscopic image 654 obtained from the fluoroscopic detector. In addition, the fluoroscopic image 654 can be positioned with respect to the body of the person 606a based on the position where the fluoroscopic image 654 is being captured from the body (e.g., using the X-ray beam). Accordingly, the fluoroscopic image 654, the image projection 656, and patient's body 606a may be aligned, so that a medical professional may see the anatomical structures of the person or patient using the image projection 656 as an overlay to the fluoroscopic image 654. The positioning and orientation of the image projection 656 and fluoroscopic image 654 may represent an AR (augmented reality) view based on a portion of a body of a person the X-ray beam is passing through (as opposed to the point of view of the medical professional).

The AR system can re-construct the 3D image data set to provide a projection from any angle that matches the position and orientation of the fluoroscopic device 654. For example, if fluoroscopic device 660 is positioned to capture a lateral view then a lateral projection of the image data set can be provided together with the lateral fluoroscopic image view. Combining and aligning of the real world view of the body of the person, image projections from the image data set, and the fluoroscopic image enable a medical professional to better view and navigate the internal anatomy of the patient. The 3D (three dimensional) image data set provides better soft tissue contrast (e.g., organs and blood vessels can be seen in the internal anatomy) and a 3D reference environment that the fluoroscopic image may not provide.

In one configuration, the fluoroscopic device 660 may be zoomed with respect to the body of the person 606a while capturing the fluoroscopic image 654. As a result, an adjustment to the image projection 656 may be performed based on a change in size of an image visible marker (i.e., a radiopaque marker 830) captured in the fluoroscopic image 654 to enable the image projection 656 to match a zoom of the fluoroscopic image 654. For example, if an image visible marker of a known size is captured (e.g., a lead marker of a defined size or length) when the fluoroscopic image 654 is zoomed in, then the amount the image projection is to be zoomed in may be determined by the visual increase in size of the image visible marker in the fluoroscopic image (or decrease in the case of zooming out). Alternatively, a zooming value may be electronically reported by the fluoroscopic device 660 or the zooming value may be provided in or with a fluoroscopic image 654, and the image projection 654 may be modified to match the fluoroscopic zoom, as electronically reported by the fluoroscopic device.

Further, as the magnification may be applied for the fluoroscopic device, there may be variations in magnification effects that may be challenging to measure directly. For example, magnification variations may occur as distances between an X-ray detector and a subject change. Thus, the radiopaque marker can be used for zoom adjustments. So, if the radiopaque marker (e.g., an L shape) is identified in a zoomed in view and the radiopaque marker is double the known physical size, then the image data set can be scaled to match the doubled size of the radiopaque marker. When the image data set is zoomed out or zoomed in, the image data set is not likely to align well with the actual view of the body of the person. As a result, the zoomed image data set and the fluoroscopic image can be aligned and displayed in an AR display 662 that is separate from the AR headset or displayed in a portion of the AR headset field of view that is not directly overlaid on the body of the person (e.g., off to the side of the center of the field of view of the AR headset).

To diminish magnification effects due to distances of patient anatomy from an X-ray source or X-ray detector, a round radiopaque sphere may be positioned at the isocenter of the patient. When magnification is used for the fluoroscopic device, the magnification may be vary depending on the distance of the body parts from the X-ray beam source. For example, the magnification of body parts that are closer to the X-ray beam source may be greater. In order to correct for these differences in magnification, the radiopaque marker used may be a metal sphere of known size (e.g., 1 cm). The metal sphere may be placed near the body part of interest (e.g., the isocenter of the image) and then the zoom of an image data set may be set to match the metal sphere. Thus, if the metal sphere appears smaller or larger in of the fluoroscopic image, the image data set can be zoomed based on that size. The metal sphere also appears the same from every angle. This appearance consistency enables the metal sphere to be an effective marker for detecting the zoom of the fluoroscopic image, which is to be applied to an image data set.

The use of an AR display 662 may also provide the ability to change a view of a fluoroscopic image and an image projection as aligned and displayed in an AR display in order to display the virtual patient to better match a position and orientation of the real view of a patient as directly viewed by a medical professional. Regardless of the orientation of the fluoroscopic image captured by the fluoroscope device, the display of the aligned fluoroscopic image and image projection can be oriented in the AR display in a way that assists the doctor and/or matches the actual view of patient's position and/or orientation. For example, the fluoroscopic image may be inverted either horizontally, vertically or oddly oriented in some other way as compared to a body of patient being actually viewed. A difficult viewing orientation may be due to the capturing orientation of the fluoroscopic device 660. Accordingly, the image with the aligned fluoroscopic image 654 and image projection 656 can be flipped or reoriented (e.g., flipped horizontally, flipped by a certain number of degrees, moved to reverse the odd orientation) for viewing by the medical professional to make a medical procedure easier to perform or match more closely with what the medical professional is seeing in an actual view. This ability to change an image orientation allows for a more intuitive interaction when performing procedures on a patient. For example, performing a medical procedure with fluoroscopic image guidance can be very difficult when everything is backwards.

Graphical indicators, virtual tools, or a virtual targeting system may also be used on the image data set or image projection to guide the position and orientation of a fluoroscopically visible object (e.g., a needle or a catheter) with respect to the body of the person and the image data set, as viewed using the AR display. Similarly, graphical indicators may be placed on the fluoroscopic image 654 to assist with guiding the fluoroscopically visible object during a medical procedure. Alternatively, the graphical indicators may be used to guide any medical implement 618 used in the fluoroscopic procedure.

Figure 8A:
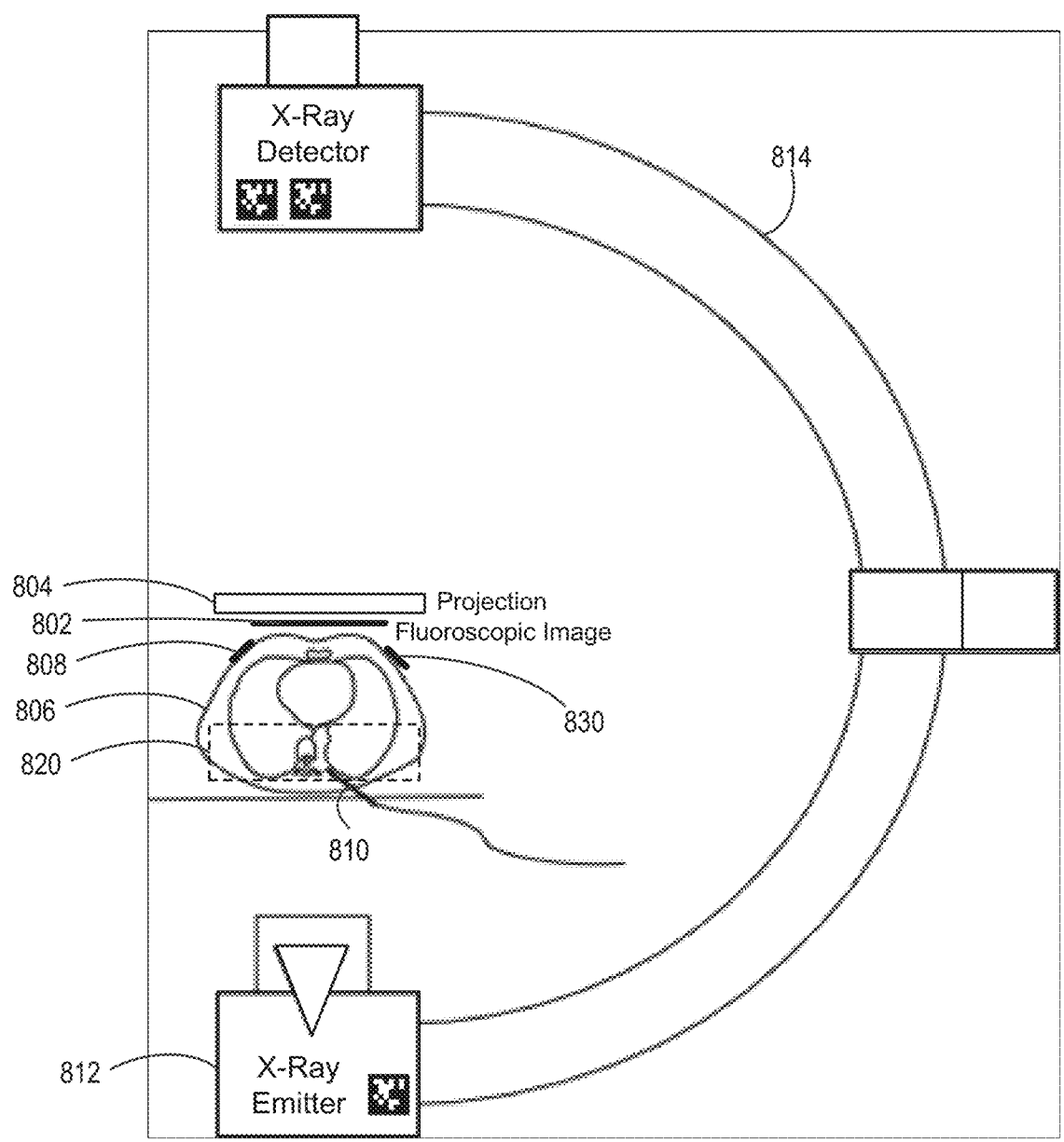
FIG. 8A illustrates a fluoroscopic device, which is mobile with respect to the body of the person, generating a fluoroscopic image and an image projection in a coronal view for the fluoroscopic device to enable combined viewing through an augmented reality (AR) headset or AR display.

FIG. 8A illustrates a side view of a combination of a cross-sectional view of a body of a person 806, an image projection 804 from an aligned image data set 820, an aligned fluoroscopic image 802 and a fluoroscopic device 814, which may enable a medical professional to fluoroscopically guide visible items 810 within a person's body 806. A fluoroscopically visible object 810 (e.g., a needle) is able to be viewed and guided by a medical professional in the fluoroscopic image 802 with respect to the image data set 820 and/or the image projection 804 aligned with the body of the person. The image projection 804 may be viewed in the AR headset or AR display as being overlaid on the fluoroscopic image 802. Alternatively, the image projection 804 may appear to have the fluoroscopic image 802 overlaid on top of the image projection 804 or the image projection 804 may appear to be within the aligned image data set 820. As discussed earlier, graphical indicators, virtual tools, or a virtual targeting system can be provided on the image data set or image projection to guide the position and orientation of the fluoroscopically visible object 810 with respect to the body of the person 806 and the image data set 820.

The transparency of the fluoroscopic image 802 aligned with the image data set may be modified depending on the amount of the image projection 804 or the real world body of the person 806 the medical professional desires to see. The fluoroscopically visible object 810 or medical implement may also have one or more optical codes on the fluoroscopically visible object 810 to be used to reference the fluoroscopically visible object 810 to the image projection 804. In addition, a position of the medical implement with respect to the body of the person and the image projection 804 or image data set 820 may be determined using optical codes on the medical implement and one or more optical codes on the body of the person 808, to enable the medical implement to be referenced to the image data and fluoroscopic image as viewed through the AR display.

The image projection 804 from an image data set 820 may have been captured using a Computed Tomography (CT) image or magnetic resonance image (MRI). Then the image projection 804 may be overlaid on a live fluoroscopic image 802. While a fluoroscopic image 802 is a live image, the fluoroscopic image does not have the 3D qualities or soft tissue contrast resolution of an MRI (magnetic resonance image) or CT (computed tomography) image. Where the fluoroscopic image 802 has been referenced to a patient's body with one or more optical codes (e.g., an AprilTag) and the projection 804 of the previously acquired 3D image data set has been referenced to an image visible tag on the patient's body, then a medical professional can view the virtual end of a needle as the tip moves in the body of the patient 806 using the AR headset or AR display. This combines valuable aspects of the virtual images, the fluoroscopic images, and a real view of a patient. A needle, a catheter tip or similar radiopaque object can be seen under fluoroscopy but the medical professional cannot see certain soft tissue in the fluoroscopic image. Thus, the combination of the real view of a patient, an image data set, a fluoroscopic image, optical tags on the fluoroscopic device, image visible tags, a medical implement, and optical tags on a medical implement may allow the medical professional to see a medical implement with reference to the image data set and/or the fluoroscopic image.

Figure 8B:
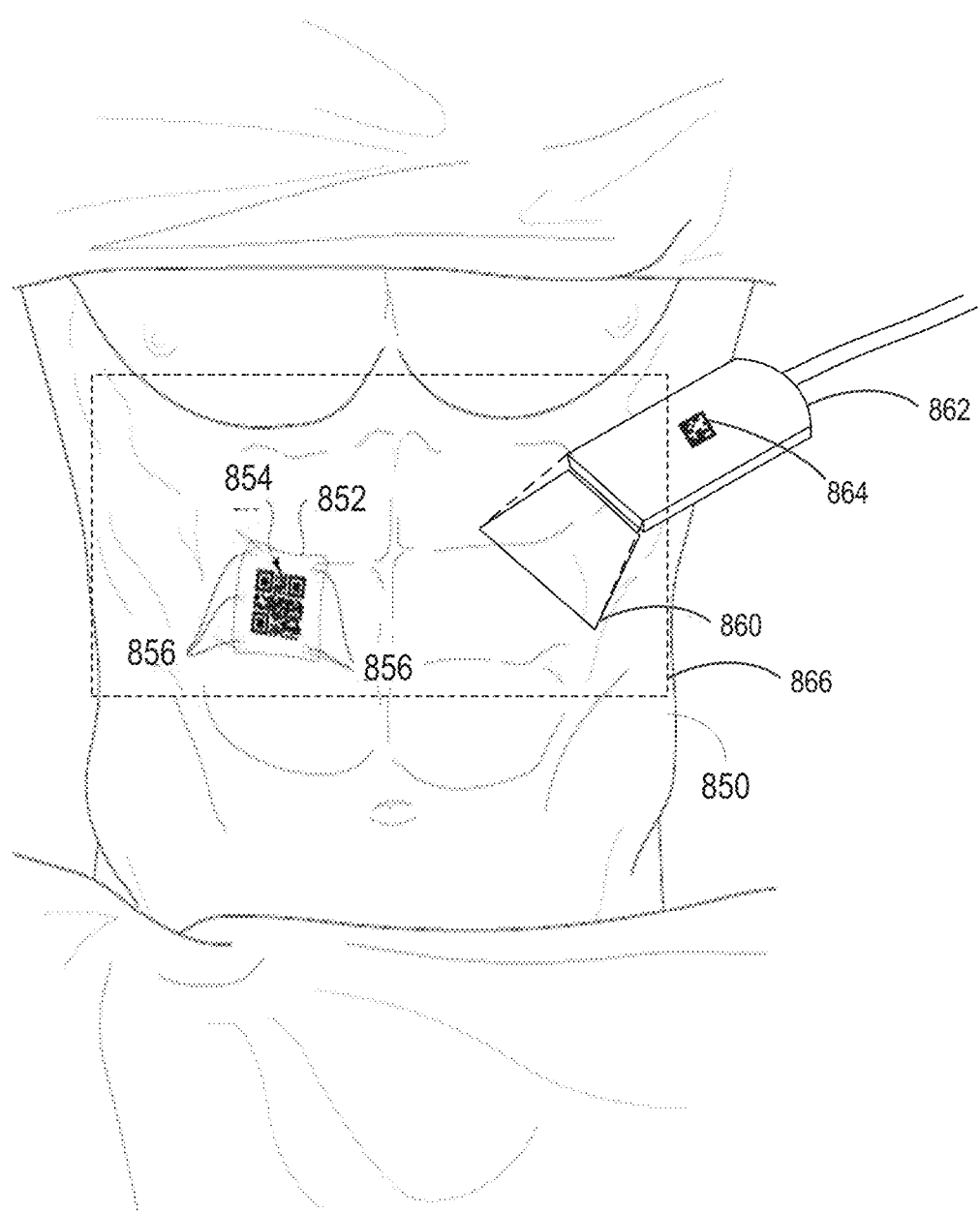
FIG. 8B illustrates an ultrasonic transducer used in combination with optical codes to enable combined viewing of image data sets and ultrasonic images through an augmented reality (AR) headset or AR display.

In another configuration, as illustrated in FIG. 8B, an ultrasound image 860 may be obtained of a portion of a body of a patient 850 using an ultrasound probe or ultrasonic transducer 862 while a medical procedure is being performed by a medical professional. The ultrasonic transducer 862 may be mobile or movable with respect to the body of the person. The ultrasound image 860 or sonogram may be a 2D, 3D or a 4D (e.g., including a time series) ultrasound image that is produced by sound waves that bounce or echo off body tissues. The echoes are processed by a computer to create the ultrasound image or sonogram.

These ultrasound images 860 may be comparatively fast and inexpensive to obtain during a medical procedure but the resolution, accuracy and localization of the ultrasound images may not be as high as other types of imaging such as CT scans, MRIs and other imaging modalities. This technology provides the ability to combine the ultrasound image 860 with other image modalities to assist a medical professional in performing a medical procedure.

Accordingly, one or more optical codes 864 may be placed on or attached to an ultrasound probe or ultrasonic transducer 862 (e.g., on the outside housing). The optical code on the ultrasound transducer 862 may be detected by the sensors in an AR headset. As a result, the position and orientation of the ultrasonic transducer 862 may be detected and the position and orientation of the ultrasound beam and the ultrasonic images can be determined based on the position and orientation of the ultrasonic transducer 862. In addition, one or more optical codes 852 on a patient or a body of a person may be detected to determine the position and orientation of the patient 850. Knowing the position and orientation of the patient 850 and the ultrasound image 860 allows the ultrasound image 860 to be aligned and projected, using the AR headset, onto a correct position on the patient. The ultrasound image 860 projected onto the patient in the AR headset may be partially transparent (e.g., using a transparency value set by the medical professional) or the ultrasound image may be opaque.

The ultrasound images 860 or a sonogram may also be combined with an image data set 866 (e.g., an MIll) which may be more accurate, clearer, higher resolution, larger, and have better tissue contrast information as compared to ultrasound images 860. As described previously, the optical codes 864 may be attached to an image visible marker 856. This image visible marker 856 may allow the image data set 866 that has been previously acquired from the patient to be aligned with the patient's body (as discussed earlier in detail). Thus, a medical professional can view the ultrasound images 860 combined with a high resolution image data set 866, as aligned and projected in the correct position on the patient's body through the AR headset or AR system. For example, if a medical professional is performing a medical procedure on a patient's liver using ultrasound equipment, a limited portion of the patient's liver may be viewed at any one time using the ultrasound images but the entire liver may be viewed using the acquired image data set along with the ultrasound images. The ultrasound image and image data set can be co-localized in the 3D space being viewed by the AR headset.

Typically, an ultrasound image 860 is not anchored to a reference point relative to the patient. Using the optical codes as described above provides a reference point within a 3D space being viewed by the AR headset. In addition, the reference points (i.e., optical codes) can be used to align the ultrasound images 860 with one or more image data sets 866.

The ultrasonic transducer may use a fan beam or a linear beam that is electronically guided. If the ultrasonic beam is moved or guided mechanically or electronically, this guidance can be taken into account when determining the location of the ultrasound image.

If a medical professional is going to perform a medical procedure such as a breast biopsy, the medical professional may use ultrasound equipment but it may be difficult to see the actual lesion in the ultrasound image. However, the lesion may be visible in the CT, MRI, PET, nuclear, or other image data set that is displayed in combination or co-localized with the ultrasound image. Thus, the ultrasound images may be used to provide images captured (e.g., in real time) during the procedure, while the previously captured detailed anatomy may be simultaneously referenced using a higher spatial or contrast resolution image data set.

The transducer may be passed over the surface of the body or inserted into an opening of a body. This may allow the fused or composite views of the ultrasound images and the image data set to provide many varying composite views of a body of a patient.

The alignment of the real time image with a body of a patient and image data sets, as described in FIG. 8B, may be applied to any type of real time medical image where the position and orientation of the real time image may be obtained from a transducer, emitter or detector of the imaging device. An additional example of such real time imaging that may be substituted for the ultrasound images is CT fluoroscopy images.

Figure 9A:
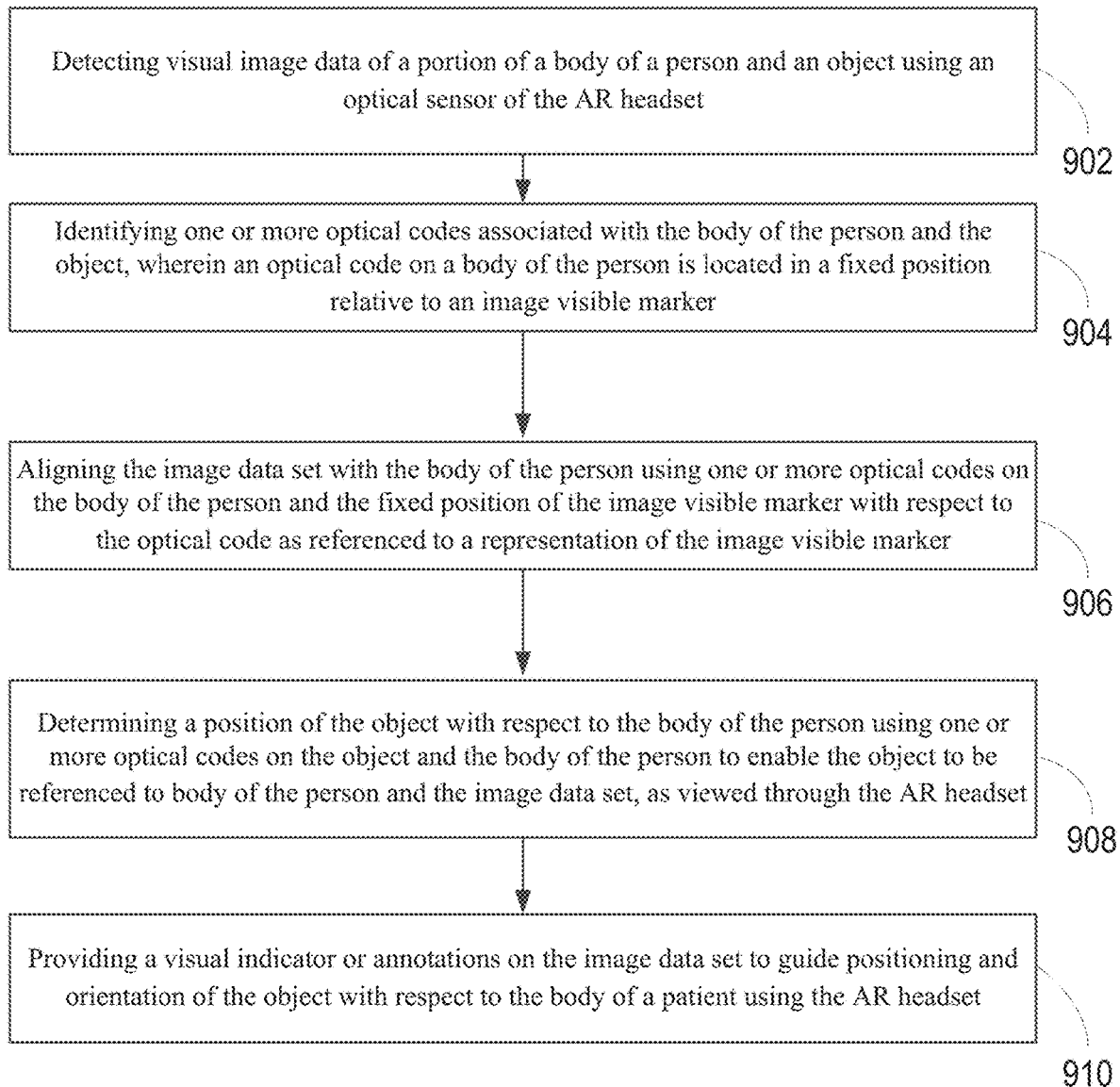
FIG. 9*a* is a flowchart of an example method of using an augmented reality headset to reference a medical implement with respect to an image data set and a body of a patient.

FIG. 9a is a flowchart of an example method of using an augmented reality headset to co-localize a medical implement with respect to an image data set and a body of a patient during a medical procedure. In these and other embodiments, the method 900 may be performed by one or more processors based on one or more computer-readable instructions stored on one or more non-transitory computer-readable media.

The method may capture visual image data of a portion of a body of a person or patient and a medical implement using an optical sensor of the AR headset, as in block 902. For example, a visible patient with an optical code is registered or detected by a camera of the AR headset used by a medical professional. One or more optical codes associated with the body of the person and the medical implement can be identified in the visual image data, as in block 904. An optical code on a body of the person may also be located in a fixed position relative to an image visible marker, as discussed earlier.

The image data set may be aligned with the body of the person using one or more optical codes on the body of the person and the fixed position of the image visible marker with respect to the optical code when referenced to a representation of the image visible marker in the image data set, as in block 906. In addition, a position and/or orientation of the medical implement with respect to the body of the person may be determined using one or more optical codes on the medical implement and the body of the person to enable the medical implement to be referenced to body of the person and the image data set, as in block 908. The alignment and merging of these multiple image aspects may be viewed through the AR headset. In one example, the image data set of radiology image can be presented at different levels of opacity depending on the needs of the user or medical professional. In addition, this opacity may be adjusted at any time.

In one configuration, the method may include providing a visual indicator, virtual guidance system, a virtual tool, a virtual highlight, or annotations on the image data set to guide positioning and orientation of the object with respect to the body of a patient using the AR headset. For example, the virtual tools or visual indicators may include one or more of: a graphical highlight, 3D colorization, a 3D surgical tract or a virtual procedural track, a graphical highlight of targeted anatomy, a graphical highlight of pathology, a graphical highlight of critical structures to avoid, or 3D visual code(s) and graphical structures (e.g., lines, planes, cylinders, volumes, boundaries, or 3D shapes) in or around an anatomical structure may also be provided (e.g., to highlight an organ or mass in the body). The method may further include mapping a contour or 3D outline of the medical implement using an optical code as the starting reference point. Further, since the position and orientation of the medical implement is known, a medical implement (e.g., a tool or implant) partially inserted into a patient's body can still be monitored by the system to ensure correct placement and positioning with respect to the image data set and ultimately the body of the person.

The method may include querying a database to determine whether the medical implement utilized or detected is assigned to be used in the medical procedure. In one example, the AR system may store medical procedure records indicating which patients are receiving specific medical procedures. These records may include a list of specific medical implements (e.g., medical instruments, implants, etc.) that are associated with individual procedures. If a medical implement is uniquely identified using an optical code, that optical code can be sent to the system and checked against the predetermined list of medical implements (each of which may be associated with separate optical codes). Thus, if an identified object is determined to be associated with the current medical procedure, a graphical indicator can be displayed representing that the medical implement is associated with the medical procedure. For example, a visible green indicator (e.g., a check mark or green medical implement highlight) may indicate a match for the procedure. In another example, a medical implement identified as being associated with the procedure may be constantly highlighted (e.g., surrounded in the AR display by a green indicator). On the other hand, if the medical implement is determined to not be associated with the current procedure then a negative visual indication may also be displayed. For example, a flashing red "X" or a red highlight outline may be a negative indicator.

The method may include displaying, in the augmented reality display, medical information associated with the medical implement. The information associated with the medical implement may include instructional information describing use of the medical implement in the medical procedure.

One issue that faces doctors and other medical professionals when performing procedures upon a patient is making sure that the correct medical implements are being used on the correct patient anatomy. If the wrong person, the wrong appendage, the wrong location, the wrong implant, is being operated or the wrong implant, wrong instrument size, or wrong medical instrument is being utilized, then a poor medical outcome may be the result. The present technology may provide an improved medical outcome by utilizing optical codes attached to medical implements.

In an additional configuration, the present technology may be used for a simulation of a medical procedure. The patient's body or patient's anatomy may be simulated using simulation structures. The simulation structures may be plastic or cadaver bones covered with soft material (plastics and rubbers to represent tissues, arteries, etc.) or other simulation materials. The simulated anatomy may include an optical code and image visible code. Then image data set for the patient on which a procedure is to be performed in the future may be aligned with the simulated anatomy.

The actual medical implements to be used in the procedure may also be included in the simulation and may be in the view of an AR headset. Similarly, a limited portion of the medical implement (e.g., just a handle of a trocar) may be used and a virtual tool in the simulated patient may be viewed. Additional overlays using real time fluoroscopy, ultrasound or other medical images captured in real time may also be used. Thus, the medical professional may perform the same functions described earlier but as a simulation in order to better understand the challenges, problems or other issues that may occur in an actual procedure that is planned. This simulation may also be used for training purposes.

Similarly, a medical trainee or an ultrasonographer may combine previously captured image data sets (e.g., MRIs or CTs images) together with actual ultrasound images being captured in real time for training purposes (as described above). It may be difficult to clearly see what is displayed in the ultrasound images due to their low spatial and contrast resolution. This may enable a medical technician to be trained about what organs, bones, blood vessels and other tissues appear like under ultrasound observation by using images with better spatial resolution and contrast resolution (e.g., MRI, CT, etc.).

Figure 9B:
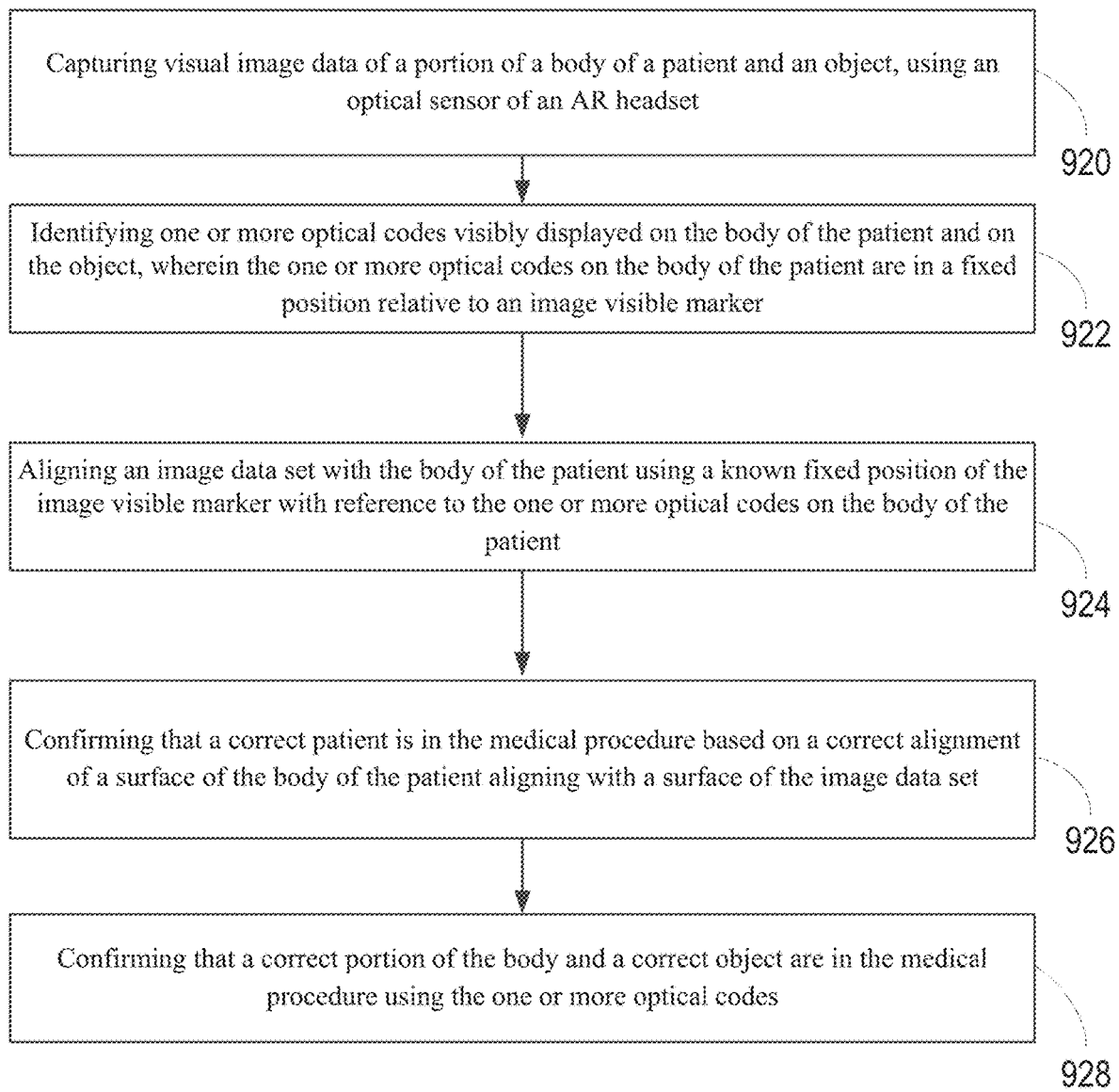
FIG. 9*b* illustrates a method for using an augmented reality (AR) display to align a fluoroscopic image, an image projection from an image data set and a body of a person using optical codes.

FIG. 9b illustrates a method for validating a medical procedure using optical codes. The method may include the operation of detecting visual image data of a portion of a body of a patient and a medical implement, using an optical sensor of an AR headset, as in block 920.

One or more optical codes visibly displayed on the body of the patient and on the medical implement may be identified, as in block 922. One or more optical codes on the body of the patient are in a fixed position relative to an image visible marker (as described earlier). An image data set may be aligned with the body of the patient using a known fixed position of the image visible marker with reference to the one or more optical codes on the body of the patient, as in block 924.

The optical codes and image visible markers may be used to confirm that a correct patient is in the medical procedure based on a correct alignment of a surface of the body of the patient aligning with a surface of the image data set, as in block 926. The surface of the body of the patient and the surface of the image data set may be created using a polygonal mesh, splines, or another mathematical model for the surface. If the surfaces (e.g., meshes) are similar or match, then the correct patient is recognized. This may be analogized to a contour type of "finger print" of the body because every individual body is unique. In addition, the identity of the person or patient in the medical procedure may also be confirmed using one or more of the optical codes. An additional function or aspect of this validation is to confirm a correct portion of the body and a correct medical implement are used in the medical procedure using one or more optical codes, as in block 928.

In a further configuration, the same optical code used during aligning the image data may be used to automatically retrieve the image data set and ensure that the image data retrieved by the AR headset matches the patient being viewed through the AR headset without time consuming, cumbersome, and inaccurate manual retrieval of image data.

Figure 10:
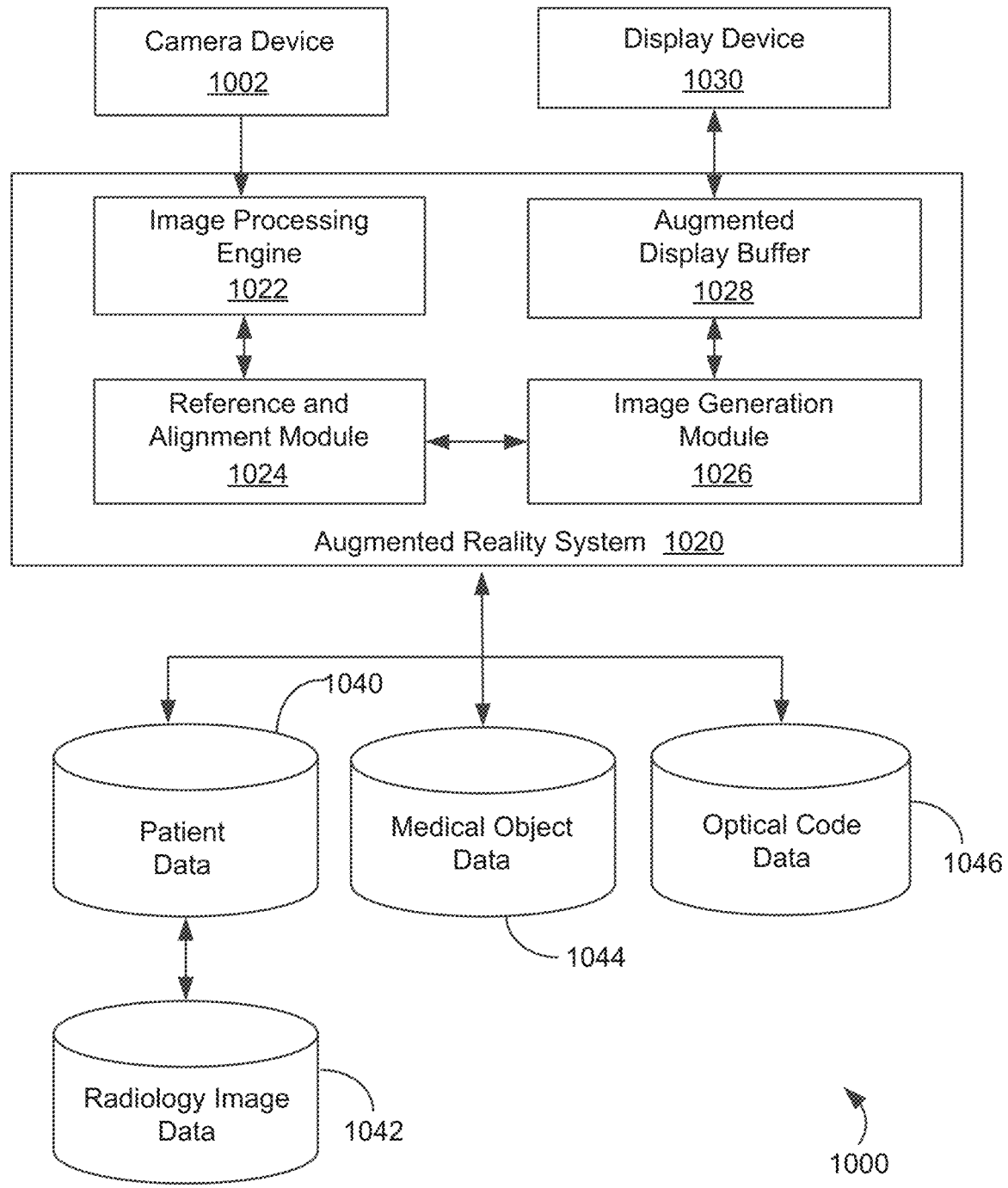
FIG. 10 illustrates an example system that may be employed in using an optical code on a medical implement to enable the medical implement to be referenced relative an image data set and to the body of a patient.

FIG. 10 illustrates an example system that may be employed to reference a medical implement to an image data set and a patient's body using optical codes, as viewed through the AR headset. The system 1000 may include a camera device 1002, an augmented reality system 1020, a display device 1030, and a plurality of databases. The system 1000 may also include one or more processors, a memory, a file system, a communication unit, an operating system, and a user interface, which may be communicatively coupled together. In some embodiments, the system 1000 may be, for example, a desktop computer, a server computer, a laptop computer, a smartphone, a tablet computer, an embedded computer, an AR headset, a VR headset, etc.

The camera device 1002 can be configured to capture visible data. In one example, the camera device 1002 may be used to capture visible data during a medical procedure. The visible data captured by the camera device 1002 may include images of a body of a person (or a portion of a body) and one or more medical implements (e.g., medical instruments, implants, and so on). The camera device 1002 may transmit the captured optical data to the augmented reality system 1020. The system also may include surface sensors, optical sensors, infrared sensors, Lidar sensors or other sensors to detect and assist with mapping a real view or actual view detected by the AR system. Any object or surface may be detected for an operating theater, a patient, a room, physical geometry, medical implements, or any other physical surroundings or objects.

The augmented reality system 1020 may include an image processing engine 1022, a reference and alignment module 1024, an image generation module 1026, and an augmented display buffer 1028. For example, the image processing engine 1022 receives the captured visible image data from the camera device 1002 and analyzes the visible image data to identify one or more optical codes, objects or people in the visible image data. A plurality of different techniques may be used to identify medical implements within the visible image data including but not limited to feature extraction, segmentation, and/or object detection.

The image processing engine 1022 also identifies optical codes that may be affixed to both bodies of patients within the image and medical implements within the visible image data. Once the image processing engine 1022 identifies an optical code (e.g., an AprilTag, a bar code, a QR code, and so on) the image processing unit 1022 accesses the optical code database 1046 to retrieve information associated with the optical code. In some examples, the optical code is associated with a particular patient, a particular procedure, or a particular object. The optical codes may be used to more accurately identify the position and orientation of the medical implement, a body or a fluoroscopic device.

In some embodiments, the reference and alignment module 1024 engages with the image processing engine 1022 to reference any identified medical implements, a body of a person and an image data set with respect to each other. In addition, the reference and alignment module 1024 can use optical code information in the medical implement database 1044 to properly identify the size and shape of the medical implements. Once the position and orientation of the medical implement and the body of the patient are determined relative to each other, the reference and alignment controller 1026 can align any associated radiology images in the radiology image data 1042 with both the body of the patient. In some examples, the radiology images are received from a radiology image database 1042 based on patient records in a patient record database 1040.

The image generation module 1026 can generate graphical data, virtual tools, a 3D surgical tract, 3D colorization or shading of a mass or organ, or highlighting of a mass, organ or target to display in a display device 1030 as layered on top of the body of the patient or a medical implement. In some examples, this information can be loaded into an augmented display buffer 1028. This information can then be transmitted to a display device 1030 for display to a user.

In one example, the patient database 1040 includes a plurality of patient records. Each patient record can include one or more medical procedures to be performed on a patient. The patient records may also include notes, instructions or plans for a medical procedure. A patient record can also be associated with one or more radiology images in the radiology image database 1042. In some examples, the radiological images include a representation of the image visible marker that allows the reference and alignment module 1026 to properly align the image data set with the body of a patient using the fixed position of an optical code with respect to the image visible marker. In some examples, the medical implement data 1044 includes information describing the medical implements, including medical instruments, implants, and other objects.

In some embodiments, the augmented reality system may be located on a server and may be any computer system capable of functioning in connection with an AR headset or display device 1030. In some embodiments, the server may be configured to communicate via a computer network with the AR headset in order to convey image data to, or receive data from, the AR headset.

Figure 11:
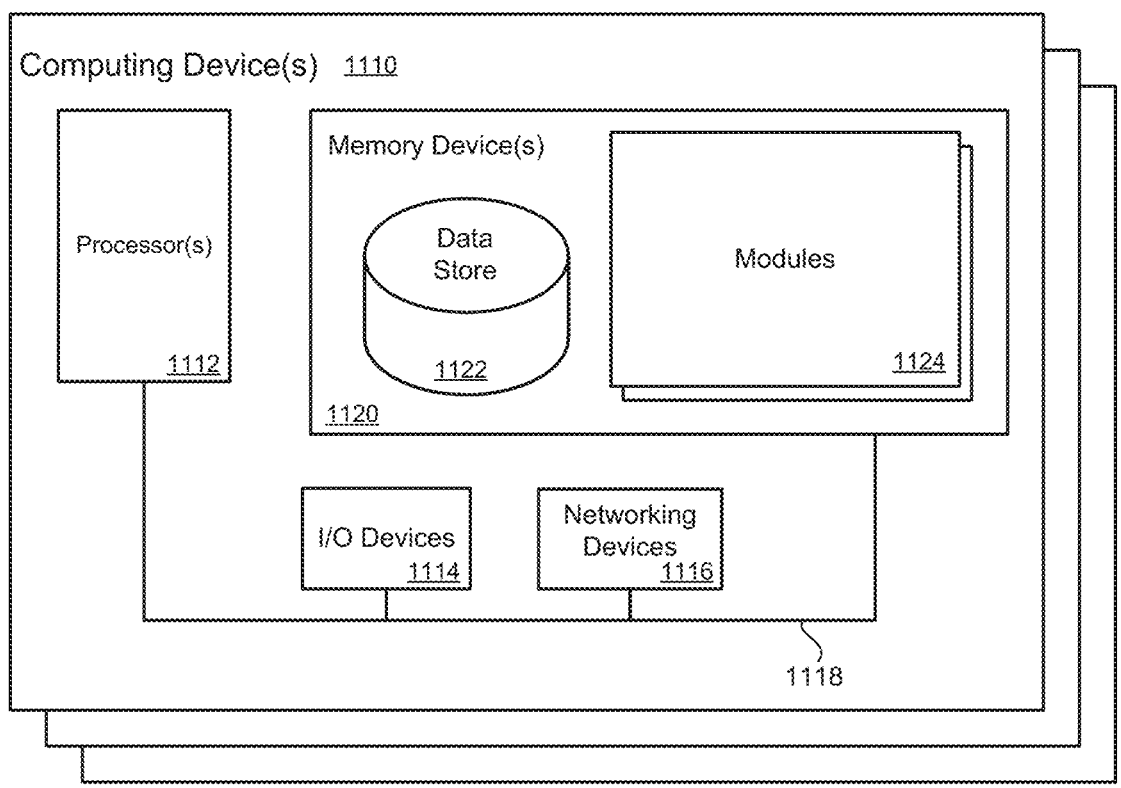
FIG. 11 is a block diagram illustrating an example of a computing system to process the present technology.

FIG. 11 illustrates a computing device 1110 on which modules of this technology may execute. A computing device 1110 is illustrated on which a high level example of the technology may be executed. The computing device 1110 may include one or more processors 1112 that are in communication with memory devices 1112. The computing device may include a local communication interface 1118 for the components in the computing device. For example, the local communication interface may be a local data bus and/or any related address or control busses as may be desired.

The memory device 1112 may contain modules 1124 that are executable by the processor(s) 1112 and data for the modules 1124. The modules 1124 may execute the functions described earlier. A data store 1122 may also be located in the memory device 1112 for storing data related to the modules 1124 and other applications along with an operating system that is executable by the processor(s) 1112.

Other applications may also be stored in the memory device 1112 and may be executable by the processor(s) 1112. Components or modules discussed in this description that may be implemented in the form of software using high programming level languages that are compiled, interpreted or executed using a hybrid of the methods.

The computing device may also have access to I/O (input/output) devices 1114 that are usable by the computing devices. An example of an I/O device is a display screen that is available to display output from the computing devices.

Other known I/O device may be used with the computing device as desired. Networking devices 1116 and similar communication devices may be included in the computing device. The networking devices 1116 may be wired or wireless networking devices that connect to the internet, a LAN, WAN, or other computing network.

The components or modules that are shown as being stored in the memory device 1112 may be executed by the processor 1112. The term "executable" may mean a program file that is in a form that may be executed by a processor 1112. For example, a program in a higher level language may be compiled into machine code in a format that may be loaded into a random access portion of the memory device 1112 and executed by the processor 1112, or source code may be loaded by another executable program and interpreted to generate instructions in a random access portion of the memory to be executed by a processor. The executable program may be stored in any portion or component of the memory device 1112. For example, the memory device 1112 may be random access memory (RAM), read only memory (ROM), flash memory, a solid state drive, memory card, a hard drive, optical disk, floppy disk, magnetic tape, or any other memory components.

The processor 1112 may represent multiple processors and the memory 1112 may represent multiple memory units that operate in parallel to the processing circuits. This may provide parallel processing channels for the processes and data in the system. The local interface 1118 may be used as a network to facilitate communication between any of the multiple processors and multiple memories. The local interface 1118 may use additional systems designed for coordinating communication such as load balancing, bulk data transfer, and similar systems.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices. The modules may be passive or active, including agents operable to perform desired functions.

The technology described here can also be stored on a computer readable storage medium that includes volatile and non-volatile, removable and non-removable media implemented with any technology for the storage of information such as computer readable instructions, data structures, program modules, or other data. Computer readable storage media include, but is not limited to, RAM, ROM, EEPROM, flash memory or other memory technology, CD-ROM, digital versatile disks (DVD) or other optical storage, magnetic cassettes, magnetic tapes, magnetic disk storage or other magnetic storage devices, or any other computer storage medium which can be used to store the desired information and described technology.

The devices described herein may also contain communication connections or networking apparatus and networking connections that allow the devices to communicate with other devices. Communication connections are an example of communication media. Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency, infrared, and other wireless media. The term computer readable media as used herein includes communication media.

Reference was made to the examples illustrated in the drawings, and specific language was used herein to describe the same. It will nevertheless be understood that no limitation of the scope of the technology is thereby intended. Alterations and further modifications of the features illustrated herein, and additional applications of the examples as illustrated herein, which would occur to one skilled in the relevant art and having possession of this disclosure, are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. One skilled in the relevant art will recognize, however, that the technology can be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements can be devised without departing from the spirit and scope of the described technology.

The invention claimed is:

1. A method for using an augmented reality (AR) headset to co-localize an image data set and a medical implement, comprising:
   detecting visual image data of a portion of a body of a person and the medical implement using an optical sensor of the AR headset;
   identifying one or more optical codes associated with the body of the person and the medical implement, wherein an optical code on a body of the person is located in a fixed position relative to an image visible marker;

confirming that the medical implement is assigned to be used in a medical procedure using the one or more optical codes;

aligning the image data set with the body of the person using the one or more optical codes on the body of the person as viewed through the AR headset and using the fixed position of the image visible marker with respect to the optical code as referenced to a representation of the image visible marker in the image data set; and determining a position of the medical implement with respect to the body of the person using the one or more optical codes on the medical implement and the body of the person to enable the medical implement to be referenced to the image data set and the body of the person, as viewed through the AR headset.

2. The method of claim 1, further comprising providing a visual indicator, a virtual tool, a virtual guidance system, a virtual highlight, a virtual procedural track, a graphical highlight of targeted anatomy, a graphical highlight of pathology, a graphical highlight of critical structures to avoid, or annotations on the image data set to guide positioning and orientation of the medical implement with respect to the body of a patient using the AR headset.

3. The method of claim 1, further comprising:
retrieving a patient's information using an optical code associated with the portion of the body of the person; and
displaying the patient's information through the AR headset to validate a correct patient and correct body part is receiving a medical procedure.

4. The method of claim 1, further comprising displaying a graphical indicator to a medical professional representing whether the medical implement is associated with the medical procedure.

5. The method of claim 1, further comprising displaying a graphical virtual implement to allow alignment of a visible implement and virtual implement.

6. The method of claim 1, further comprising retrieving medical information associated with the medical implement that includes instructional information describing use of the medical implement in a medical procedure.

7. The method of claim 1, wherein the medical implement is a medical instrument, a trocar, a catheter, a needle, orthopedic hardware, or a surgical implant.

8. The method of claim 1, further comprising mapping a contour of the medical implement using the one or more optical codes on the medical implement as a starting reference point.

9. The method of claim 1, further comprising retrieving the image data set automatically for the body of the person using the one or more optical codes on the body of the person.

10. A method for using an augmented reality (AR) display to align a fluoroscopic image with respect to a body of a person and an image projection from an image data set, comprising:

detecting visual image data of a portion of the body of a person and a fluoroscopic device, which is mobile with respect to the body of the person, using an optical sensor of the AR display;

identifying one or more optical codes on the body of the person and on the fluoroscopic device, wherein one or more optical codes on the body of the person have a fixed position relative to an image visible marker;

aligning an image data set of the body of the person using the fixed position of the image visible marker relative to the one or more optical codes on the body of the person as viewed through the AR display;

determining a position and orientation of the fluoroscopic device with respect to the body of the person using the one or more optical codes on the fluoroscopic device;

generating an image projection of the image data set based in part on the position and orientation of the fluoroscopic device;

displaying the image projection through the AR display; and displaying a fluoroscopic image from the fluoroscopic device that is aligned with the body of the person and the image projection based on the image visible marker or the position and orientation of the fluoroscopic device, using the AR display.

11. The method as in claim 10, further comprising:
detecting a change in the position and orientation of a fluoroscopic device with respect to the body of the person; and
modifying the image projection and fluoroscopic image position and orientation as defined by the change in position and orientation of the fluoroscopic device.

12. The method as in claim 10, wherein adjusting a position of the image projection, as viewed by the AR display, is based on a change in position and orientation of the fluoroscopic device as detected using the one or more optical codes on the fluoroscopic device as compared to a position and orientation of the body of a patient.

13. The method as in claim 10, further comprising:
receiving a zoom value from the fluoroscopic device that has been zoomed with respect to the body of the person; and
adjusting the image data set as defined by a zoom value of the fluoroscopic device.

14. The method as in claim 13, wherein adjusting the image data set is performed based on using a size of the image visible marker captured in the fluoroscopic image to enable the image data set to match a zoom of the fluoroscopic image.

15. The method as in claim 10, wherein a fluoroscopically visible object in the fluoroscopic image is able to be viewed and guided by a medical professional with respect to the image data set aligned with the body of the person.

16. The method of claim 10, further comprising providing graphical indicators, virtual tools, or a virtual targeting system on the image data set to guide the position and orientation of a fluoroscopically visible object with respect to the body of the person and the image data set, as viewed using the AR display.

17. The method of claim 10, wherein determining an orientation of the fluoroscope device further comprises determining a position and orientation of the fluoroscope device with respect to the body of the person.

18. The method of claim 10, further comprising reconstructing the image projection of the image data set and moving the fluoroscopic image, as viewed in the AR display, corresponding to a change in orientation and position of the fluoroscope device.

19. The method of claim 10, wherein a transparency of the fluoroscopic image aligned with the image data set may be modified.

20. The method as in claim 10, further comprising:
identifying one or more additional optical codes visibly displayed on a medical implement; and determining a position of the medical implement with respect to the body of the person and the image projection using the one or more additional optical codes on the medical implement and the one or more optical codes on the body of the person, to enable the medical implement to be referenced to the image data, as viewed through the AR display.

21. A method for using an augmented reality (AR) display to align a fluoroscopic image with respect to a body of a person that has one or more optical codes by using a position and orientation of a fluoroscopic device that has one or more optical codes, comprising:

identifying the one or more optical codes on the body of the person and on the fluoroscopic device, which is mobile with respect to the body of the person, using an optical sensor of the AR display;

determining the position and orientation of the fluoroscopic device with respect to the body of the person using the one or more optical codes on the fluoroscopic device; and displaying, using the AR display, a fluoroscopic image from the fluoroscopic device aligned with the body of the person by referencing the optical codes on the body of the person and the position and orientation of the fluoroscopic device.

22. The method as in claim 21, further comprising:
identifying one or more optical codes on the body of the person which have a fixed position relative to an image visible marker;

aligning an image data set of the body of the person using the fixed position of the image visible marker relative to the one or more optical codes on the body of the person, as viewed through the AR display; and displaying the image data set through the AR display as aligned with the body of the person and with the fluoroscopic image.

23. The method as in claim 22, further comprising:
generating an image projection of the image data set based on the position and orientation of the fluoroscopic device; and displaying the image projection through the AR display, as aligned with the body of the person, with the fluoroscopic image.

24. The method as in claim 23, wherein the image projection may be reconstructed based on movement of the fluoroscopic device to match a changed position of the fluoroscopic device.

25. The method as in claim 21, further comprising generating an image projection of an image data set based on the position and orientation of a viewer who is using an AR headset.

26. A method for using an augmented reality (AR) display to align an ultrasonic image with respect to a body of a person, comprising:

detecting visual image data of a portion of the body of a person and a ultrasonic transducer using an optical sensor of the AR display;

identifying one or more optical codes on the body of the person and on the ultrasonic transducer;

determining a position and orientation of the ultrasonic transducer with respect to the body of the person using the one or more optical codes on the ultrasonic transducer; and displaying an ultrasonic image from the ultrasonic transducer that is aligned with the body of the person by referencing the one or more optical codes on the body of the person and the position and orientation of the ultrasonic transducer, using the AR display.

27. A method for validating a medical procedure using optical codes:

detecting visual image data of a portion of a body of a patient and a medical implement, using an optical sensor of an AR headset;

identifying one or more optical codes visibly displayed on the body of the patient and on the medical implement, wherein the one or more optical codes on the body of the patient are in a fixed position relative to an image visible marker;

aligning an image data set with the body of the patient using a known fixed position of the image visible marker with reference to the one or more optical codes on the body of the patient;

confirming that a correct patient is in the medical procedure based on a correct alignment of a surface of the body of the patient aligning with a surface of the image data set; and confirming that a correct portion of the body and a correct medical implement are in the medical procedure using the one or more optical codes.

28. The method of claim 27, further comprising retrieving patient data for display in the AR headset using the one or more optical codes.

29. The method of claim 27, further comprising providing annotations on the image data set to guide position and orientation of the medical implement with respect to the body of the patient and the image data set using the AR headset.

* * * * *